(12) United States Patent
Markussen et al.

(10) Patent No.: US 9,233,209 B2
(45) Date of Patent: Jan. 12, 2016

(54) MEDICAL INJECTION DEVICE

(75) Inventors: Tom Hede Markussen, Bagsvaerd (DK); Freddy Verner Michelsen, Aastorp (SE); Bo Radmer, Hilleroed (DK); Knud Skifter Winther, Snekkersten (DK); Claus Urup Gjoedesen, Copenhagen O (DK); Christian Hoejris Nielsen, Copenhagen NV (DK); Martin Majdall Petersen, Oelstykke (DK); Jesper Peter Windum, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 120 days.

(21) Appl. No.: 13/818,827

(22) PCT Filed: Aug. 29, 2011

(86) PCT No.: PCT/EP2011/064846
§ 371 (c)(1),
(2), (4) Date: May 6, 2013

(87) PCT Pub. No.: WO2012/025639
PCT Pub. Date: Mar. 1, 2012

(65) Prior Publication Data
US 2013/0218093 A1    Aug. 22, 2013

Related U.S. Application Data

(60) Provisional application No. 61/378,694, filed on Aug. 31, 2010.

(30) Foreign Application Priority Data

Aug. 27, 2010    (EP) .................................... 10174354

(51) Int. Cl.
*A61M 5/315* (2006.01)
*A61M 5/00* (2006.01)
(Continued)

(52) U.S. Cl.
CPC .......... *A61M 5/31501* (2013.01); *A61M 5/001* (2013.01); *A61M 5/002* (2013.01);
(Continued)

(58) Field of Classification Search
CPC .......... A61M 5/31501; A61M 5/3202; A61M 5/2466; A61M 5/001; A61M 5/2033; A61M 5/002; A61M 5/326; A61M 2005/2086; A61M 2005/31518; A61M 2005/206; A61M 2005/3118; A61M 2005/247
USPC ......... 604/131, 134–135, 148, 181, 186–187, 604/207–208, 212, 214, 232, 234, 244–246
See application file for complete search history.

(56) References Cited

U.S. PATENT DOCUMENTS 3,528,404 A * 9/1970 Chan .................... A61B 5/1427
600/575
4,986,818 A    1/1991 Imbert et al.
(Continued)

FOREIGN PATENT DOCUMENTS

EP    0516473 A1    2/1996
EP    1138338 A1    10/2001
(Continued)

*Primary Examiner* — Amber Stiles
(74) *Attorney, Agent, or Firm* — Leon Y. Lum

(57) ABSTRACT

The present invention relates to injection devices for injecting a medicament from a cartridge (600) through a needle cannula (510). The injection device (100) includes an actuator (330, 360) for driving a piston driver (310) and includes an end of stroke limiter (341, 611). When the piston driver (310) is arrested by the end of stroke limiter (341, 611) a shielding driver (370) is automatically triggered to actively shift the needle cannula (510) into a shielded state. The injection device may include a fluid dispensing interruption mechanism that automatically interrupts fluid flow when the piston driver has moved a predetermined stroke length. The injection device may also include a single pre-stressed spring acting exclusively in a linear compression mode or exclusively in a torsion mode and adapted to sequentially drive the device to enable fully automatic operation. The invention also relates to a method of sterilizing a needle cannula assembly.

11 Claims, 26 Drawing Sheets

Figures 1C, 1D:
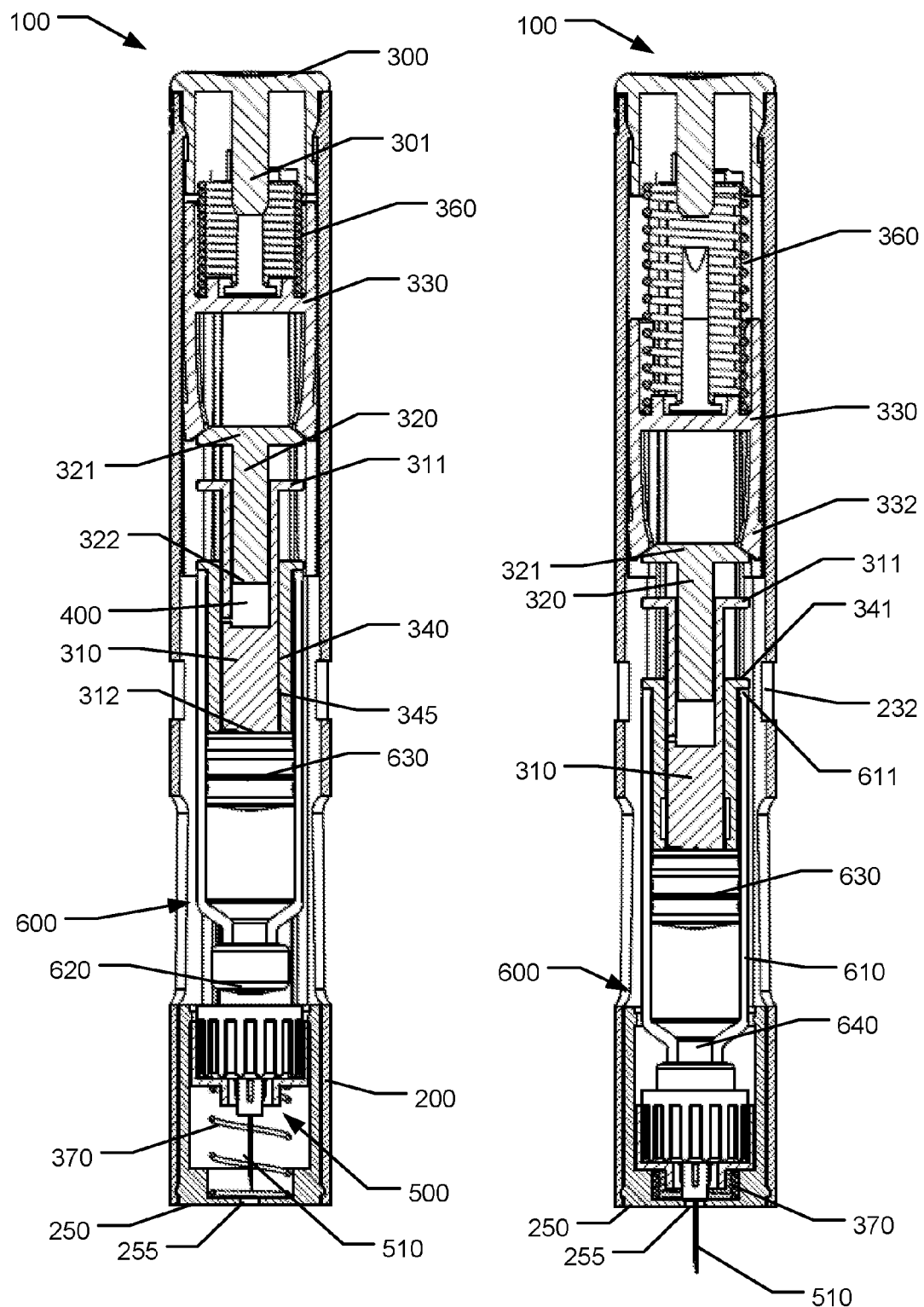

(51) Int. Cl.
*A61M 5/20* (2006.01)
*A61M 5/32* (2006.01)
*A61M 5/24* (2006.01)
*A61M 5/31* (2006.01)

(52) U.S. Cl.
CPC .......... *A61M 5/2033* (2013.01); *A61M 5/2466* (2013.01); *A61M 5/3202* (2013.01); *A61M 5/326* (2013.01); *A61M 2005/206* (2013.01); *A61M 2005/2086* (2013.01); *A61M 2005/247* (2013.01); *A61M 2005/3118* (2013.01); *A61M 2005/31518* (2013.01)

(56) References Cited

U.S. PATENT DOCUMENTS

| | | | |
|---|---|---|---|
| 5,658,259 A * | 8/1997 | Pearson | A61M 5/2033 604/136 |
| 2002/0007671 A1 | 1/2002 | Lavi et al. | |
| 2003/0105430 A1 | 6/2003 | Lavi et al. | |
| 2007/0276338 A1 * | 11/2007 | Shue et al. | 604/187 |
| 2008/0312592 A1 | 12/2008 | Barrow-Williams et al. | |
| 2010/0049125 A1 | 2/2010 | James et al. | |

FOREIGN PATENT DOCUMENTS

| | | | |
|---|---|---|---|
| EP | 1743666 | A1 | 1/2007 |
| FR | 2905273 | A1 | 3/2008 |
| WO | 97/14455 | A1 | 4/1997 |
| WO | 03/092771 | A1 | 11/2003 |
| WO | 03/097133 | A1 | 11/2003 |
| WO | 2004/054645 | A2 | 7/2004 |
| WO | 2005/077441 | A2 | 8/2005 |
| WO | 2005/115516 | A1 | 12/2005 |
| WO | 2006/062997 | A1 | 6/2006 |
| WO | 2008/020023 | A1 | 2/2008 |
| WO | 2008/029280 | A2 | 3/2008 |
| WO | 2008/065646 | A1 | 6/2008 |
| WO | 2008/148518 | A1 | 12/2008 |
| WO | 2009007305 | A1 | 1/2009 |
| WO | 2009/063030 | A1 | 5/2009 |
| WO | 2009062509 | A1 | 5/2009 |

* cited by examiner

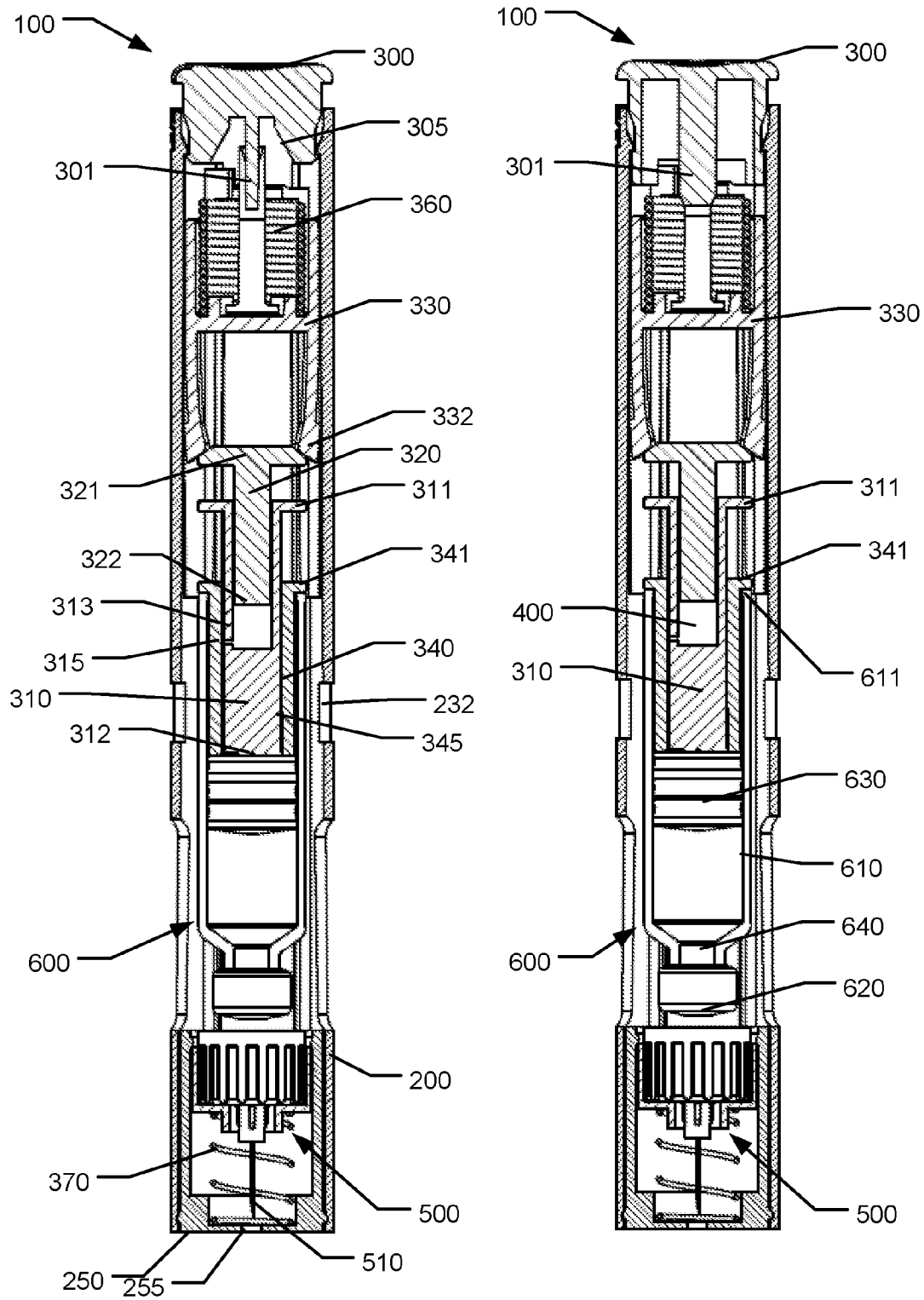

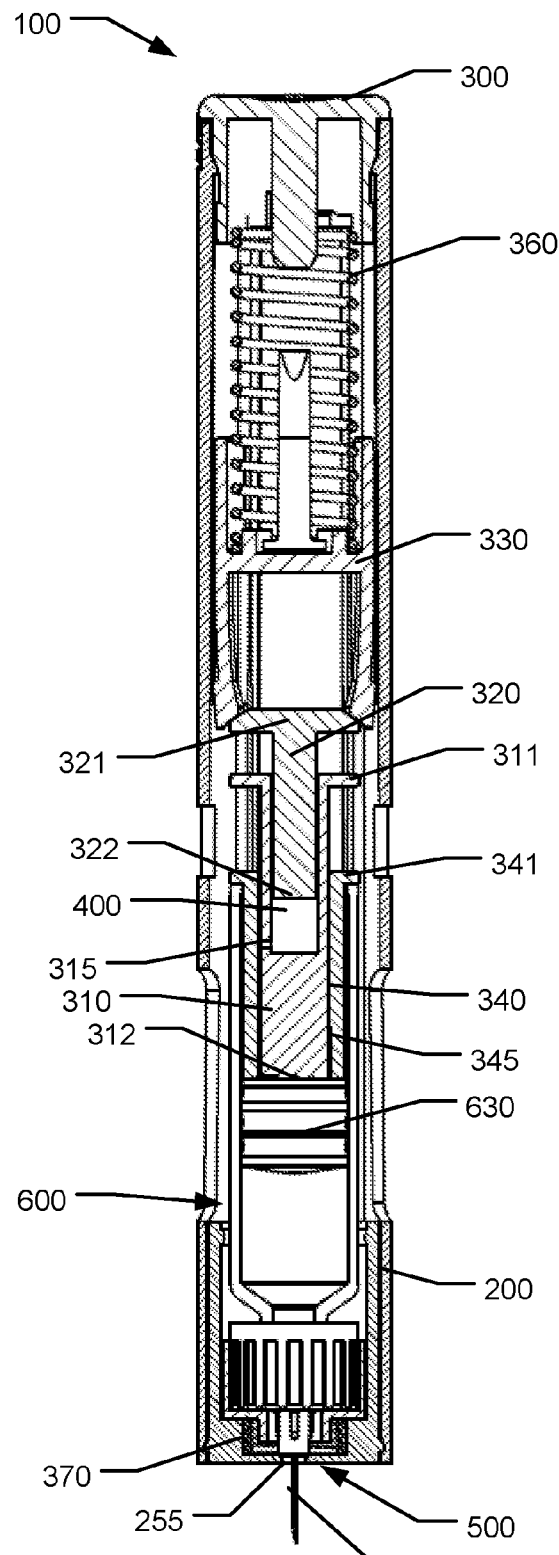
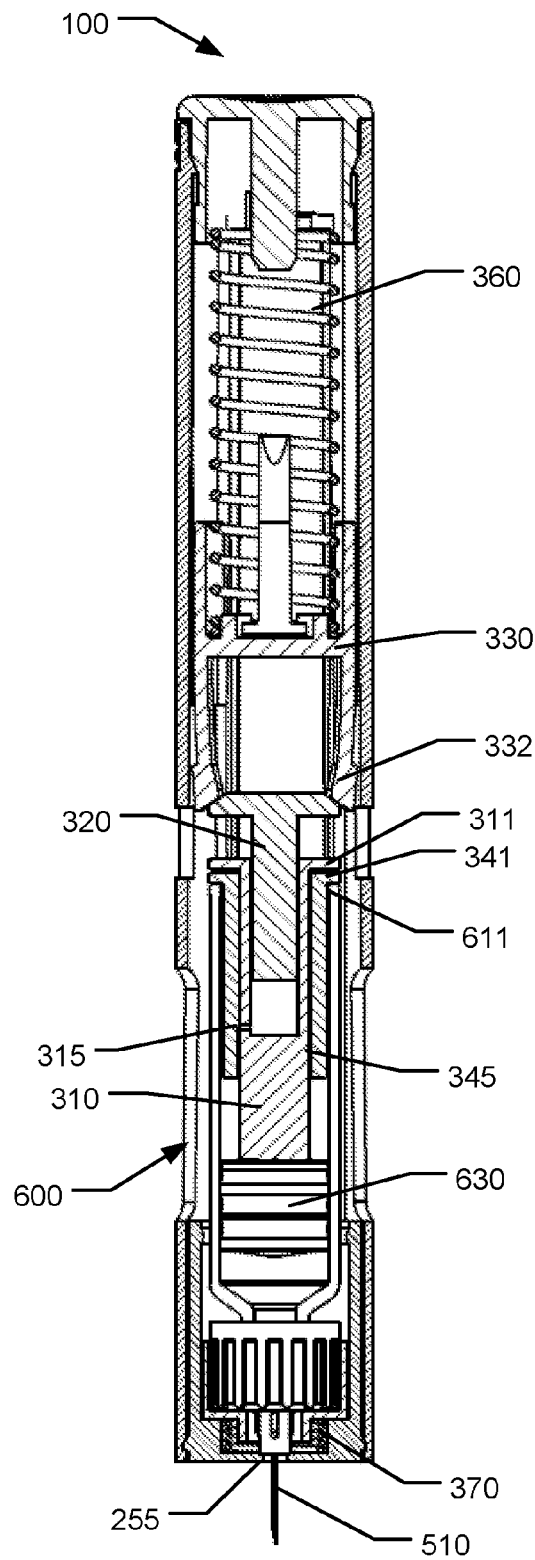
Fig. 1e
Fig. 1f

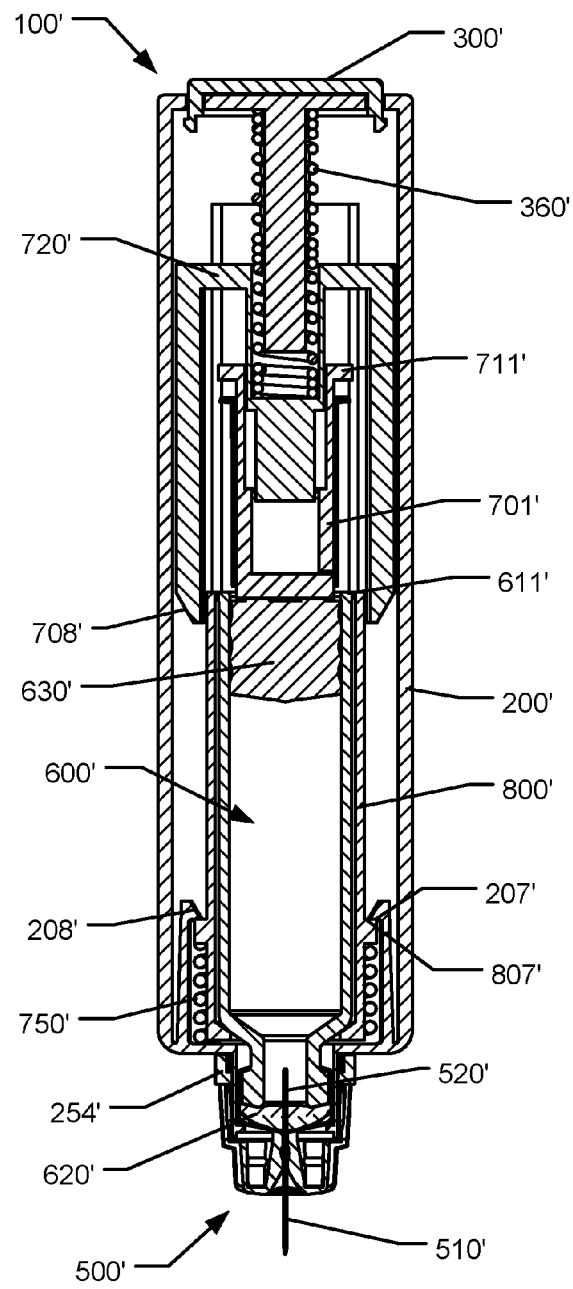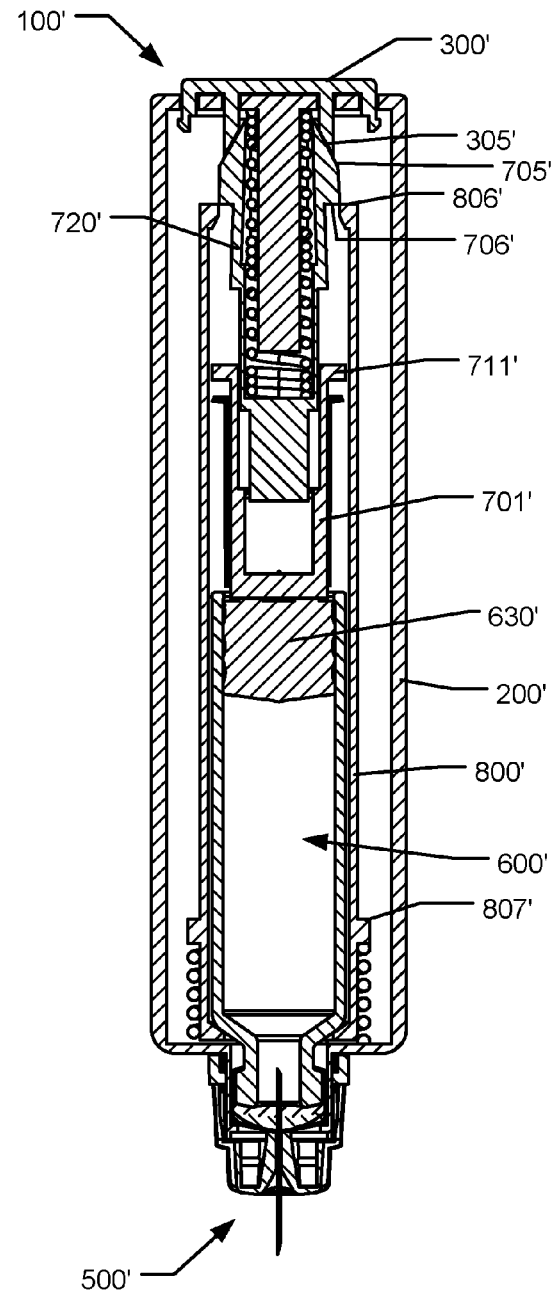
Fig. 6c
Fig. 6d

MEDICAL INJECTION DEVICE

CROSS-REFERENCE TO RELATED APPLICATIONS

This application is a 35 U.S.C. §371 National Stage application of International Application PCT/EP2011/064846 (WO 2012/025639), filed Aug. 29, 2011, which claimed priority of European Patent Application 10174354.0, filed Aug. 27, 2010; this application claims priority under 35 U.S.C. §119 of U.S. Provisional Application 61/378,694; filed Aug. 31, 2010.

FIELD OF THE INVENTION

The present invention relates to injection devices for injecting a medicament. In particular the present invention relates to injection devices for injecting a medicament from a held cartridge and improvements relating to the performance of such injection devices.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed that makes the use of an injection device as simple as possible. Such devices are typically designed such that a user shall position the injection device onto the injection site and activate the device. Such activation causes the device to insert a needle into the skin, eject a dose of the medicament and subsequently move the needle into a shielded position.

An example of such a device is shown in EP516473A1 which employs a powerful spring that, when released, thrusts forward the piston of a syringe to thereby project the needle of the syringe in the flesh of the patient and subsequently thrust forward the piston inside the syringe to expel the medicament. At the end of this phase the spring is automatically decoupled from the piston, leaving the syringe free to be acted upon by a relatively weak return spring, which urges the syringe to a retracted position to thereby shield the needle.

As identified in WO 03/097133, an injection device of the above type, have a problem with dosage delivery due to length tolerances of the syringe and due to the exact trigger point for triggering of the needle retraction being very much dependent on the length of the syringe. WO 03/097133 attempts to alleviate this problem by introducing a two part piston drive where the two parts of the piston drive are connected by means of a damper mechanism. This ensures that the piston is moved all the way to the needle end of the syringe before triggering the needle retraction sequence. However, due to the damping system is initiated upon the initial actuation of the device, the point in time where the needle retraction actually is initiated is not well defined relative to the point in time where the piston impacts the internal end walls of the syringe. This may still lead to inaccurate delivery and/or prolonged waiting time for an administration to be completed. In related auto-injectors such as disclosed in WO 03/092771 and WO 2008/029280 similar problems apply.

In other injection devices, such as the ones disclosed in WO 2006/062997, the piston stroke of a cartridge is mainly controlled by using a rear part of the cartridge to define both the start point for the piston and the end of stroke point where the expelling movement is interrupted. The disclosed injectors provide auto penetration and auto expelling features but require manual withdrawal of the needle from the skin subsequent to an injection.

When using injectors where the patient is responsible for manually removing the needle from the skin after the end of an injection, the patient is generally requested to leave the needle inserted for 6 to 10 seconds, or even longer after the end of stroke condition, to ensure that the complete desired amount of injectable fluid is actually injected. During this time, the system relaxes and a small amount of drug will be forced out through the needle. This effect is partly attributable to the fact that during the dosing procedure, the piston deforms, which results in the actual travelled distance of the front face of the piston being different than the travelled distance of the piston driver immediately after the piston driver has travelled the predetermined distance. After the piston driver has stopped its movement the piston will return to its original shape, thus ejecting the remainder of the medicament. This phenomenon is causing some inconvenience for the user. He needs to keep the needle in the skin for a relatively long time in order to fully receive the intended dose.

In a further reference, WO 2008/020023, the problem of drooling from the needle after an injection procedure is addressed by proposing to release the pressure on a piston rod of the device shortly after injection. In addition, this reference proposes to include a valve at the delivery opening of the device for preventing drooling at the end of a delivered dose. Both solutions result in unnecessary complex devices.

Having regard to the above-identified prior art devices, it is an object of the present invention to provide an injection device which minimizes the time that the needle need to be inserted into the skin, yet obtaining a large degree of dosing accuracy and automation.

For injection devices, in particular for single shot injectors, different references in the art proposes to incorporate injection needles of the type having a penetrable sterility sheath which encircles the needle cannula at least along a part of the extension of the cannula. The sterility seal of such injection needles enables penetration by the pointed tip of a needle cannula, when the sterility sheath is moved against the pointed tip. Such injection needles typically offer a minimum of required handling steps during the act of administering a dose. However, this kind of injection needles typically require that each injection needle, during manufacture, is handled separately from other injection needles in order not to accidentally penetrate the sterility sheath. It is a further object of the present invention to provide a cost-effective sterilization and handling process for such injection needles.

Yet additional further objects of the invention are to provide measures for obtaining devices having superior performance and, at the same time, enabling manufacture at a reduced cost.

BRIEF DESCRIPTION OF THE INVENTION

In a first aspect, the present invention relates to an injection device comprising:
a) a medicament cartridge having a body extending from a proximal end to an outlet formed at a distal end, said body comprising a proximally facing surface, wherein the outlet is connectable to or connected to a needle cannula and wherein a slideably arranged piston is driveable in the distal direction from an initial predetermined position relative to the proximally facing surface,
b) a piston driver for engaging the piston and capable of driving the piston a pre-determined stroke length towards the distal end of the cartridge, c) an actuator providing a stored energy source capable of being released to cause the piston driver to drive the piston in the distal direction,
d) a needle shielding portion associated with the needle cannula, the needle shielding portion and the needle cannula being configured for relative movement from an unshielded state where the needle cannula protrudes from the needle shielding portion into a shielded state where the needle cannula is shielded, and
e) an end of stroke limiter for arresting the piston driver in a pre-determined position relative to said proximally facing surface of the cartridge,
wherein the injection device further comprises a triggerable shielding driver which upon triggering is adapted to actively shift the injection device from the unshielded state to the shielded state, said shielding driver being automatically triggered upon the piston driver being arrested by the end of stroke limiter.

According to the first aspect of the invention, by configuring the device with a precise dosing mechanism having an accurate pre-determined stroke length and which offers monitoring of the exact point in time where the end of stroke condition has occurred, this enables the use of an automatic needle shielding process which is accurately triggered relatively to the end of stroke condition. When administering a dose with such a device, the time that the needle need to be inserted into the skin after the dosing operation can be minimized, yet obtaining a large degree of dosing accuracy and automation.

The cartridge may be of the type having a pierceable septum intended for being pierced by a needle cannula. In other embodiments, the cartridge is of the type where a needle cannula is fixedly attached to the body of the cartridge. The piston of the cartridge may generally define a longitudinal axis along which the piston moves.

In some embodiments the actuator comprises a spring, such as a compression spring or a torsion spring. The spring may in some embodiments be a constant force spring configured to drive forward the piston driver with a near-constant force.

The injection device may include an actuator connector which couples the actuator with the piston driver, wherein the actuator connector is configured to move the piston driver during the injection stroke until the piston driver is arrested by the end of stroke limiter whereupon the actuator connector is capable of movement relative to the piston driver for triggering the shielding driver to shift the injection device from the unshielded state to the shielded state.

The injection device may be so configured so that the actuator connector is only translationally movable relative to the piston driver after the piston driver has been arrested relative to the cartridge body. Hence the actuator connector substantially follows axial movements of the piston driver during a substantial part of the stroke where the piston driver moves relative to cartridge body.

In some embodiments, the piston driver is locked relative to the actuator connector during said substantial part of the stroke. After this point in time, the actuator connector is released relatively to the piston driver allowing the actuator connector to move relative to the piston driver and hence to cooperate in triggering the shielding driver. Said release may be configured to occur after 50% of said stroke where the piston driver moves relative to cartridge body, such as after 60%, such as after 70%, such as after 80%, such as after 90%, such as after 95%, such as after 98% of said stroke.

In some embodiments the relative movement of the actuator connector and the piston driver is controlled by a damper comprising a variable volume reservoir having a viscous fluid therein and having a control valve through which the viscous fluid escapes as the volume of the variable volume reservoir decreases, wherein the control valve is being configured to open substantially at the point in time where the end of stroke limiter arrests the piston driver, such as less than such as less than 4 secs before the end of stroke limiter arrests the piston driver, such as less than 3 secs before, such as less than 2 secs before, such as less than 1 sec before, such as less than 0.8 secs before, such as less than 0.5 secs before, such as less than 0.2 secs before the end of stroke limiter arrests the piston driver.

The actuator connector and the piston driver may jointly define said variable volume reservoir.

The injection device may in some embodiments further include a release mechanism for releasing said stored energy source from acting on the actuator connector upon the variable volume reservoir being reduced to a pre-defined volume to thereby trigger said shielding driver.

The damper may in some embodiments be configured to release the release mechanism within 4 seconds, preferably within 2 seconds, more preferably within 1 second and most preferably within 0.5 seconds after said control valve is opened.

In other embodiments the relative movement of the actuator connector and the piston driver is controlled by a mechanical lock which releases at the point in time where the end of stroke limiter arrests the piston driver, such as less than such as less than 4 secs before the end of stroke limiter arrests the piston driver, such as less than 3 secs before, such as less than 2 secs before, such as less than 1 sec before, such as less than 0.8 secs before, such as less than 0.5 secs before, such as less than 0.2 secs before the end of stroke limiter arrests the piston driver.

A bushing element may be inserted in a proximal opening of the cartridge wherein the bushing element comprises a rim section which abuts or may be brought to abut the proximal end face of the cartridge and wherein the end of stroke limiter is defined by said rim section. The piston driver may thus become halted when the piston driver abuts the rim section of the bushing element which further abuts the proximal end face of the cartridge.

In embodiments where the device includes a damper mechanism, such bushing element and the piston driver may jointly define said control valve.

Said proximally facing surface of the cartridge may be a proximal end face of the cartridge, whereby the proximal end face defines said end of stroke limiter. The end of stroke limiter then cooperates with the piston driver to accurately stop the piston driver from moving further in the distal direction either by direct abutment or by abutment via one or more intermediary components.

The shielding may in some embodiments include a shield spring configured for urging the needle cannula and the needle shielding portion into its shielded state. In such embodiments, the force acting on the piston driver and emanating from said stored energy source upon energy release may be larger than the spring force of the shield spring. Said force emanating from the stored energy source may be >200% of the force of the shield spring, preferably 200%-150% of the force of the shield spring, more preferably 150%-125% of the force of the shield spring, most preferably >100% of the force of the shield spring.

In some embodiments, the shielding process for shielding the front needle of the needle cannula may utilize a configuration where the needle cannula is withdrawn relative to a needle shielding portion associated with a housing of the device. In other embodiments, the shielding process for shielding the front needle of the needle cannula may utilize a configuration where a needle shield, which is movable relative to a main housing of the device, subsequent to the end of stroke condition is thrust forward relatively to the needle cannula to thereby effectively push away the remaining part of the device from the injection site.

The injection device may further comprise an activation button that must be initially turned to unlock the device for subsequent operation of the activation button, such as by pressing the button to activate the actuator. In order to unlock the device the button must be turned >360° around its axis, preferably 180°-360° around its axis, more preferably 90°-180° around its axis, most preferably >45° around its axis.

According to a second aspect of the invention, an auto-injection device is provided which comprises:

a) a medicament cartridge having an outlet covered by a cartridge septum adapted to be pierced by a needle for establishing fluid communication with the cartridge interior and having a slideably arranged piston which is driveable towards the outlet, b) a piston driver for engaging the piston and capable of driving the piston a predetermined stroke length towards the outlet of the cartridge, c) needle holding means and, optionally, a needle assembly mounted on said needle holding means, said needle assembly having a front needle for penetrating the skin of a subject user and a rear needle for piercing the cartridge septum, the cartridge and the needle assembly being configured for relative movement between a first state where the cartridge septum is pierced by the rear needle and where fluid communication is enabled into a second state where said fluid communication is interrupted, and d) an actuator coupled to the piston driver and driveable, when the cartridge septum is pierced by the rear needle, to cause the piston driver to move to dispense the medicament from the front needle in a dispensing operation, wherein the injection device further comprises a dispensing interruption mechanism adapted to actively shift by means of a relative movement the cartridge and the needle assembly from the first state wherein the cartridge septum is pierced by the rear needle and wherein fluid is dispensable from the front needle into the second state where fluid flow from the cartridge to the rear needle is interrupted responsive to the piston driver having moved the piston said predetermined stroke length to thereby automatically interrupt the dispensing operation. According to the second aspect, by providing an injection device with a dispensing interruption mechanism which is configured to separate the cartridge and the needle rapidly after an end of stroke condition, the duration of the administration procedure can be shortened as the user will not have to wait for the relaxation of the piston of the cartridge at the end of stroke condition. At the same time the usability of the device is more intuitive as the user is allowed to remove the device from the skin at the time of feedback, such feedback being a tactile or audible or visual feedback signalling the end of stroke condition. User compliance can be increased as users who remove the device before relaxation of piston will be in compliance. In addition, potential back flow from the skin to the cartridge is avoided as the connection between needle and cartridge is stopped.

The dispensing interruption mechanism may comprise biasing means adapted to urge the cartridge and the needle assembly towards the second state where said fluid communication is interrupted. The dispensing interruption mechanism may include a retainer adapted to releasably retain the cartridge and the needle assembly in the state where the cartridge septum is pierced by the rear needle.

The cartridge may be mounted slideably relative to the housing for moving the cartridge away from the needle assembly upon release of said retainer. The piston of the cartridge may be mounted to the piston driver thereby fixing the cartridge slidably to the piston driver.

The dispensing interruption mechanism may further include a retainer release trigger being associated with the piston driver and being adapted to cooperate with a retainer release surface associated with the retainer and adapted to release said retainer when the piston driver has moved into a predetermined position.

In some embodiments the device further comprises a housing wherein the cartridge is retained in a cartridge holder mounted slideably relative to the housing for moving the cartridge away from the needle assembly.

The actuator may include a stored energy source capable of being released to cause the piston driver to move to dispense the medicament through the needle assembly.

The stored energy source may be a single pre-stressed spring acting exclusively in a linear compression mode or exclusively in a torsion mode and wherein a force transfer mechanism transfers the force of the spring upon release sequentially in a first direction for:

a) driving the piston driver for dispensing a dose of the medicament of the cartridge through the needle assembly, and in a second direction for:

b) driving the cartridge relative to the needle assembly from the first state wherein the cartridge septum is pierced by the rear needle and wherein fluid is dispensable from the front needle into the second state where fluid flow from the cartridge to the rear needle is interrupted.

The device may further include an end of stroke limiter for arresting the piston driver in a pre-determined position relative to said proximally facing surface of the cartridge. The said end of stroke limiter may be defined by a proximal facing surface of the cartridge.

In further embodiments, the piston driver comprises a first part which is coupled to the piston of the cartridge and a second part which is configured to move the first part during the injection stroke until the first part is arrested relative to the cartridge by means of the end of stroke limiter whereupon the second part is capable of further movement relative to first part for triggering release of said retainer.

In some embodiments the relative movement of said first and second part of the piston driver is controlled by a damper mechanism. Said damper mechanism may be adapted to include any of the features described in accordance with the first aspect above.

The end of stroke limiter may be defined by the first part of the piston driver. In such an embodiment the first part of the piston driver comprises a distal facing surface defining one part of the end of stroke limiter for cooperating with the proximal end of the cartridge either directly or via a bushing element as described in connection with the first aspect above.

According to a third aspect of the invention, an auto-injection device is provided, comprising:

a medicament cartridge having an outlet connectable or connected to a needle cannula and having a slideably arranged piston which is driveable towards the outlet to dispense a dose of medicament, a needle shielding portion associated with the needle cannula, a piston driver for engaging the piston and capable of driving the piston in a distal direction towards the outlet of the cartridge, a needle cannula which is movable between a shielded state where the needle tip of the needle cannula is shielded by the needle shielding portion and an unshielded state where the needle tip protrudes from the needle shielding portion, a single pre-stressed spring which upon release acts to drive the injection device sequentially for:
a) driving the needle cannula from the shielded state and into the unshielded state,
b) driving the piston driver for dispensing a dose of the medicament of the cartridge through the needle cannula, and
c) driving the needle cannula from the unshielded state into the shielded state, wherein the spring is a single pre-stressed spring acting exclusively in a linear compression mode or exclusively in a torsion mode and wherein a force transfer mechanism transfers the force of the spring upon release sequentially in a first direction for:
a) driving the needle cannula from the shielded state and into the unshielded state, and
b) driving the piston driver for dispensing a dose of the medicament of the cartridge through the needle cannula,
and in a second direction for:
c) driving the needle cannula from the unshielded state into the shielded state.

According to the third aspect, by providing the auto-injector with a single pre-stressed spring acting exclusively in a linear compression mode or exclusively in a torsion mode and with a force transfer mechanism that utilizes the spring force for transferring movement of the parts for obtaining a fully automatic operation of all the operating sequences, a particularly cost effective design is obtained.

According to a fourth aspect of the invention, an auto-injection device is provided, comprising:
a medicament cartridge having an outlet defined by a cartridge septum adapted to be pierced by a needle for establishing fluid communication with the cartridge interior and having a slideably arranged piston which is driveable towards the outlet,
optionally, a needle assembly having a front needle for penetrating the skin of a subject user and a rear needle for piercing the cartridge septum, the cartridge and the needle assembly being configured for relative movement from a first state where the cartridge septum is sealed to a second state where the cartridge septum is pierced by the rear needle,
a needle shielding portion associated with the needle assembly,
a piston driver for engaging the piston and capable of driving the piston towards the outlet of the cartridge,
a single pre-stressed spring acting either exclusively in a linear compression mode or exclusively in a torsion mode to drive the injection device sequentially for:
a. driving the needle cannula relative to the needle shielding portion for shifting the front needle from a shielded state and into an unshielded state,
b. driving the piston driver for dispensing a dose of the medicament of the cartridge through the needle cannula, and
c. driving the cartridge (600') relative to the needle assembly (500') from the first state wherein the cartridge septum (620') is pierced by the rear needle (520') and wherein fluid is dispensable from the front needle (510') into the second state where fluid flow from the cartridge (600') to the rear needle is interrupted.

According to the fourth aspect, the operational principle of a device according to the second aspect and the cost effectiveness of a device according to the third aspect, the respective benefits of these kinds of devices may be combined in one and the same injection device.

Any of the features mentioned in connection with the second and third aspect and which logically combines with a device according to the fourth aspect defined above may be used in combination with the invention according to the fourth aspect.

Embodiments according to the first and third aspects include variants having a cartridge and a needle assembly being configured to connect either during manufacture or during use to establish fluid communication between the cartridge and the needle cannula. Other embodiments include variants where the cartridge is provided as a cartridge container and a needle cannula that is formed as an integral unit during manufacture. Some variants may use cartridge made of glass. Other embodiments may use a cartridge container being made of a synthetic resin or the like. In addition some embodiments may use a cartridge having a cartridge body which at the same time performs as a housing.

Each of the devices of the first, second, third and fourth aspects may be formed as disposable (single use) devices which in one form may be adapted to deliver a single dose of a medicament for subsequent disposal. Such devices may have a medicament cartridge irremovably accommodated inside a housing.

According to a fifth aspect of the invention, a method of sterilizing a needle cannula assembly is provided, the method comprising the steps of:
a) providing an injection needle comprising:
a needle hub,
a first needle cannula part mounted in the needle hub and extending towards a pointed tip, and
a first needle sheath associated with the first needle cannula part, the first needle sheath being formed as a flexible sheath configured as a closed cavity for accommodating at least a part of said first needle cannula part extending beyond the pointed tip of the first needle cannula part and fully or partly towards the needle hub, the first needle sheath being configured to be penetrated by the pointed tip of the first needle cannula part upon relative movement between the first needle sheath and the first needle cannula part,
b) providing a sterilizing compartment for the injection needle and inserting the injection needle therein to form a needle assembly, the sterilizing compartment forming a rigid structure to at least partly accommodate the first needle sheath of the injection needle and having at least one sterilizing opening, said needle assembly being formed so that the first needle sheath is prevented from moving relative to the first needle cannula when bulk handling the needle assembly and one or more additional similar needle assemblies so as to avoid accidental penetration of the first needle sheath by the pointed tip of the first needle cannula,
c) repeating steps a and b to form a plurality of needle assemblies,
d) arranging said plurality of needle assemblies in bulk, and
e) bulk sterilizing the plurality of needle assemblies.

The sterilizing compartment may be so formed that the first needle sheath of the needle assembly is prevented from being touched by any other of the needle assemblies irrespective of their relative orientation.

The type of injection needle may be of the kind which further comprises:
- a second needle cannula part mounted in the needle hub and extending towards a pointed tip in a direction opposite to said first needle cannula part,
- a second needle sheath associated with the second needle cannula part, the second needle sheath being formed as a flexible sheath configured as a closed cavity for accommodating said second needle cannula part and extending beyond the pointed tip of the second needle cannula part and fully or partly towards the needle hub, the second needle sheath being configured to be penetrated by the pointed tip of the second needle cannula part upon relative movement between the second needle sheath and the second needle cannula part, and wherein said sterilizing compartment further forms a rigid structure to at least partly accommodate the second needle sheath of the injection needle so that the second needle sheath is prevented from moving relative to the second needle cannula part when bulk handling the needle assembly and one or more additional similar needle assemblies.

The sterilizing compartment may be so formed that also the second needle sheath of the needle assembly is prevented from being touched by any other of the needle assemblies irrespective of their relative orientation.

According to the fifth aspect, by utilizing a sterilizing compartment for each injection needle and forming the sterilizing compartment and the injection needle in a way which ensures that the needle sheaths of each needle cannula assembly is not touched by other needle cannula assemblies when handled in bulk, it is ensured that the needle sheaths are not accidentally urged to move relative to the pointed tip section of the respective needle cannula part. Hence, the risk of accidental sheath penetration is significantly reduced even when plural such needle cannula assemblies are sterilized by means of a bulk sterilization process and the sterility of the needles is kept uncompromised while yet the cost connected to the sterilizing process is significantly reduced. Moreover, safety during handling is improved.

The first and/or the second needle sheath of the injection needle may be formed by an elastomeric material such as being made of a penetrable rubber material.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 1G:
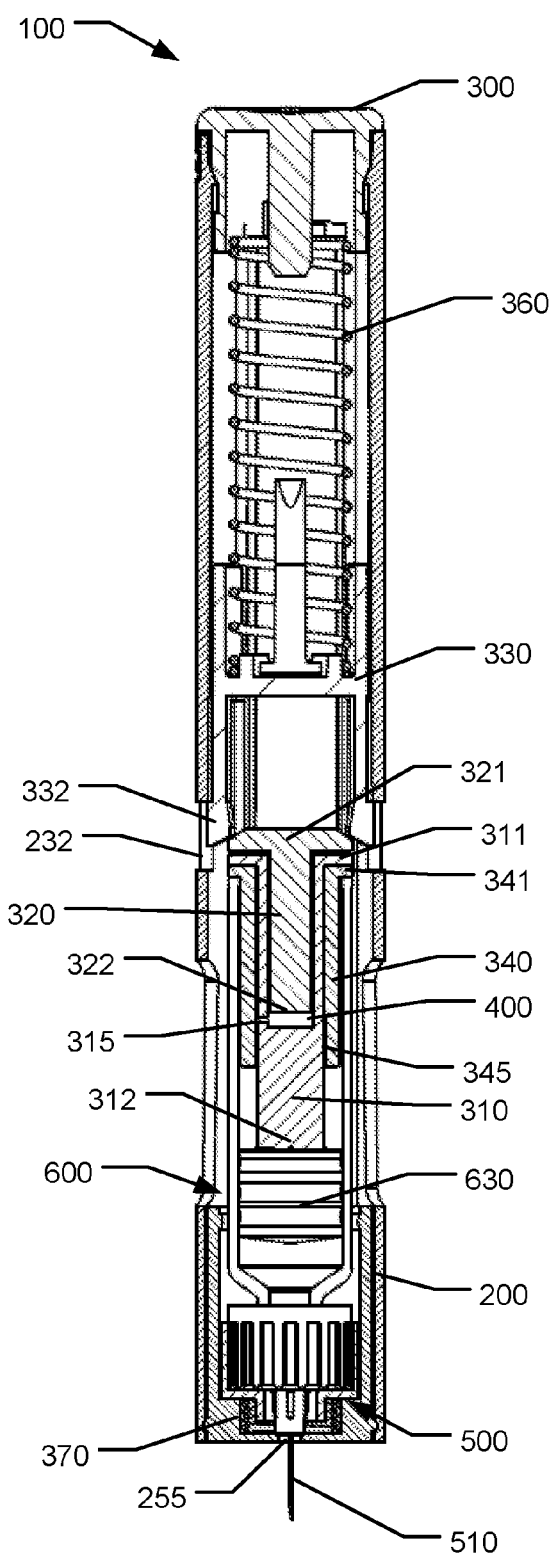
Figure 1H:
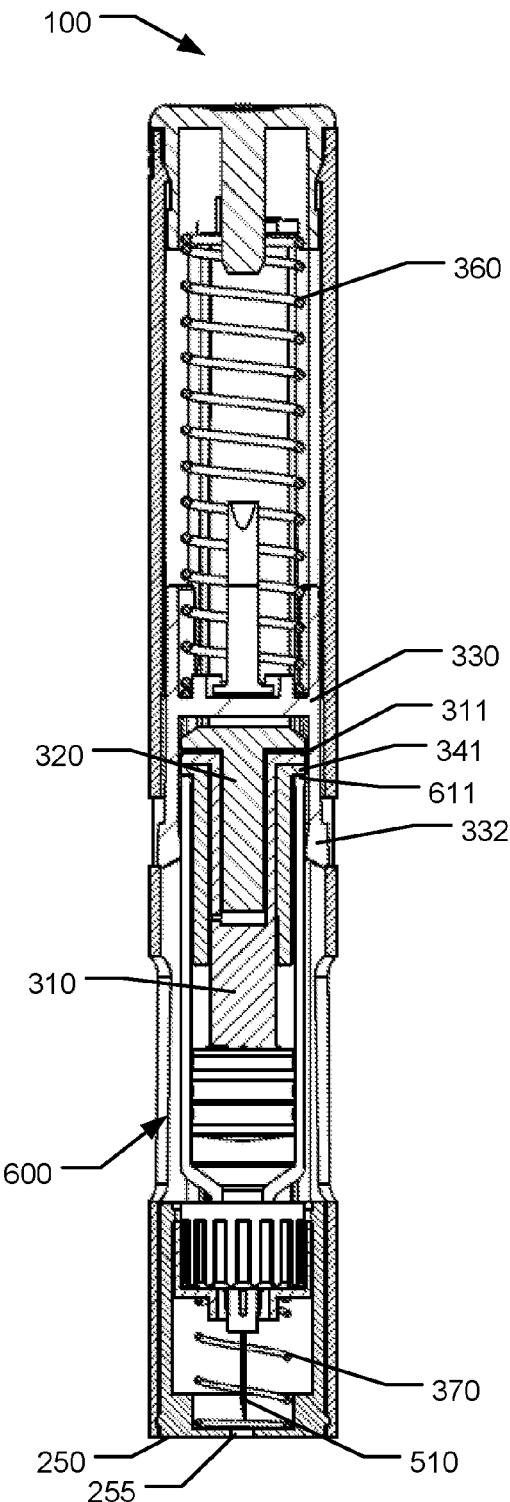
Figure 2:
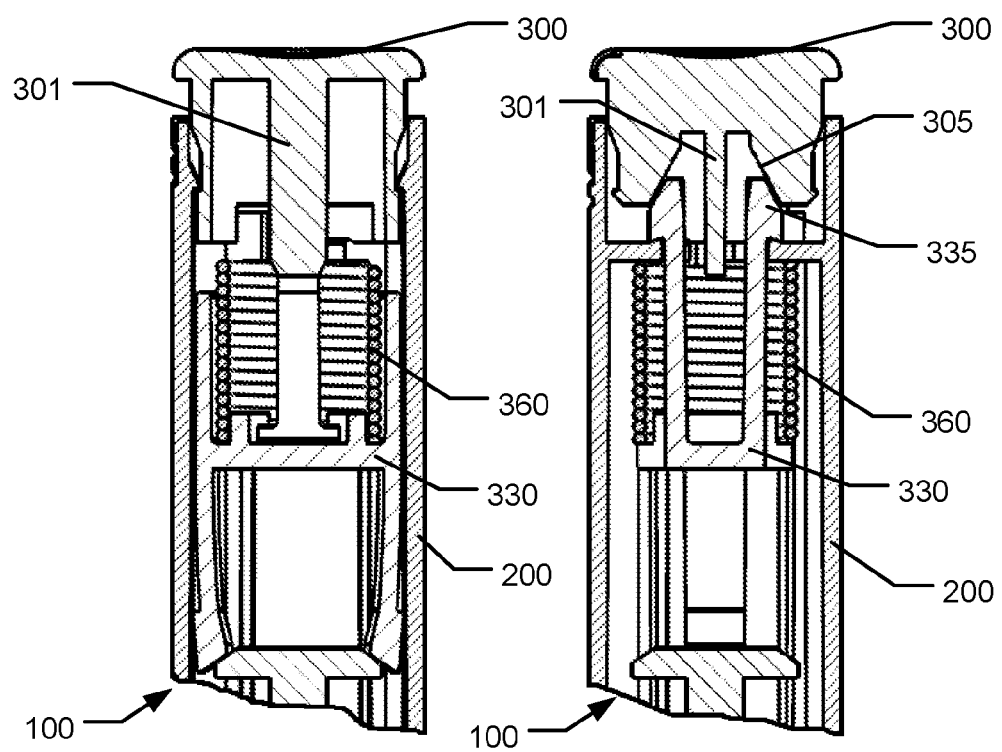
Figure 3:
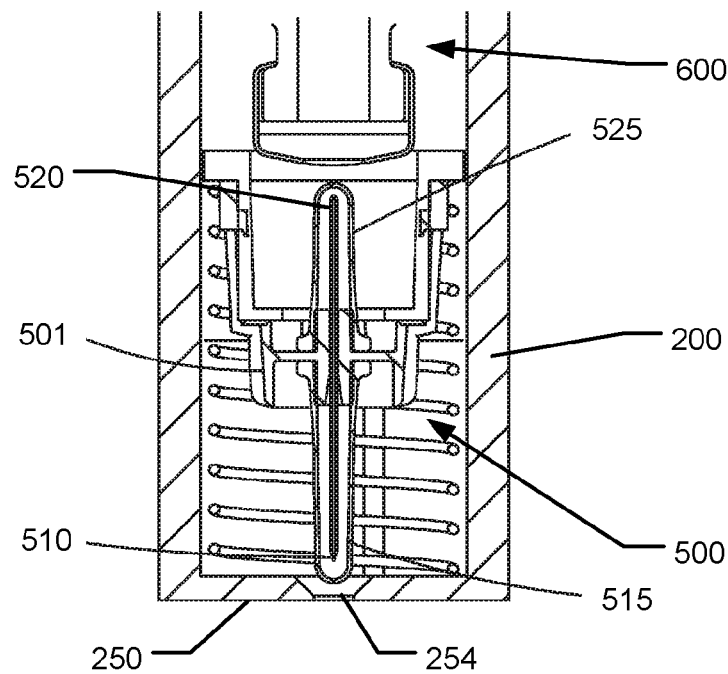
Figure 4A:
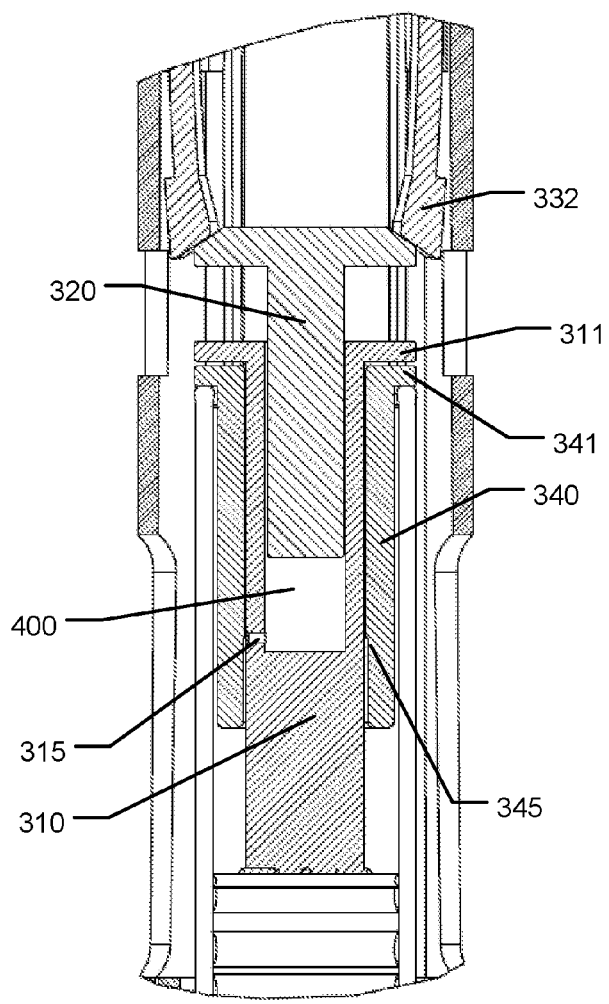
Figure 4B:
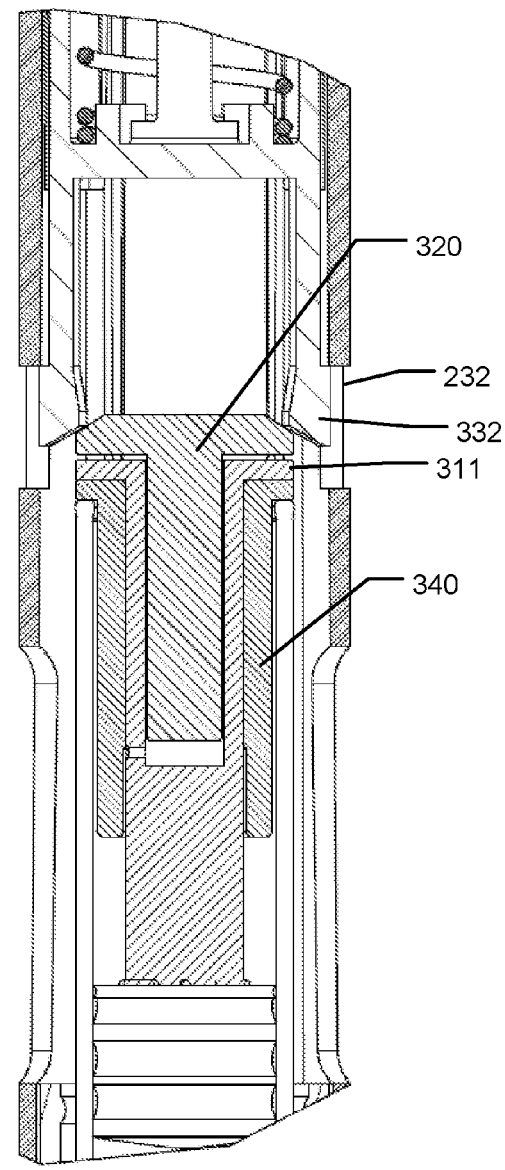
Figures 10A, 10B, 10C, 10D:
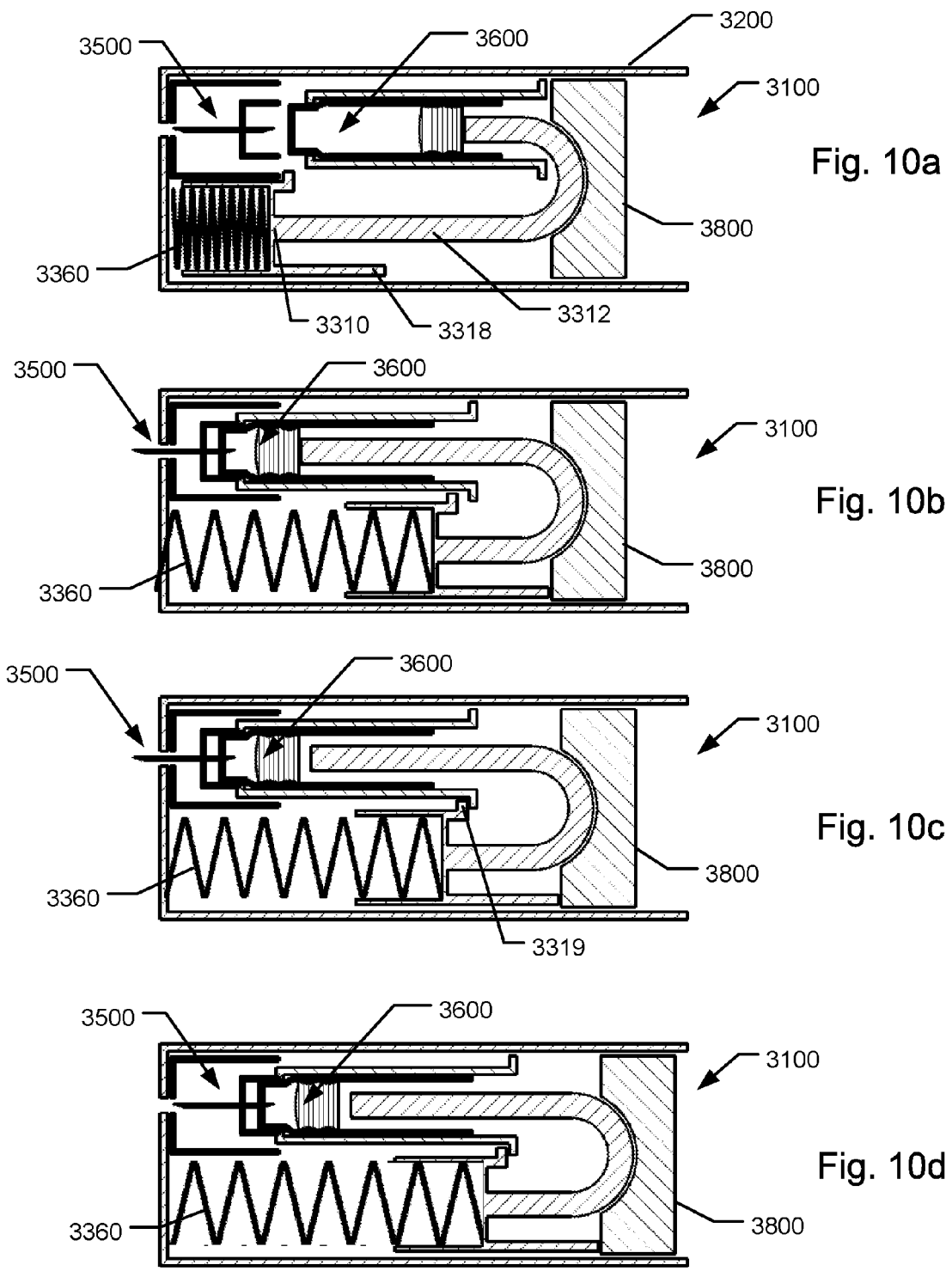
Figure 11A:
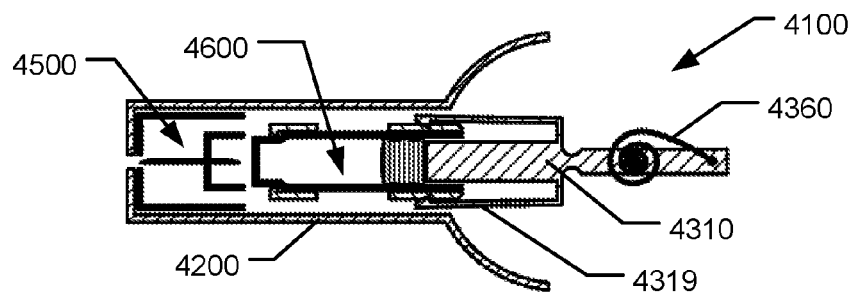
Figure 11B:
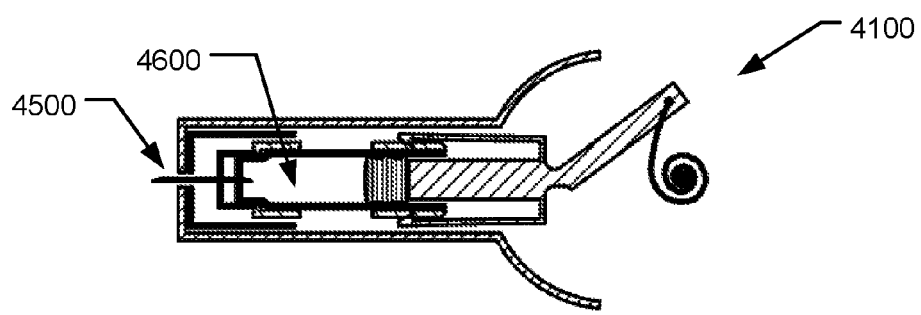
Figure 11C:
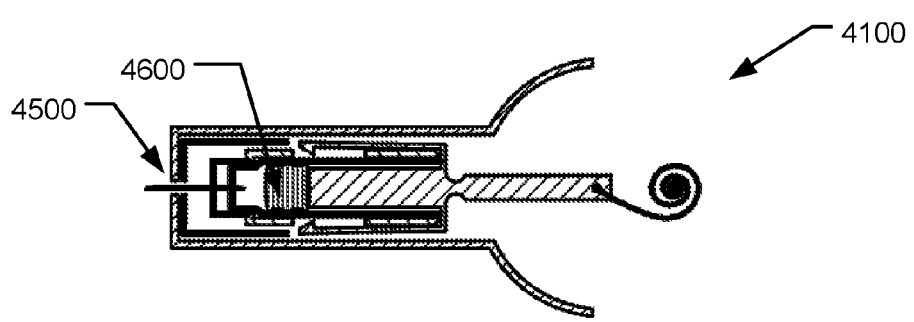
Figure 11D:
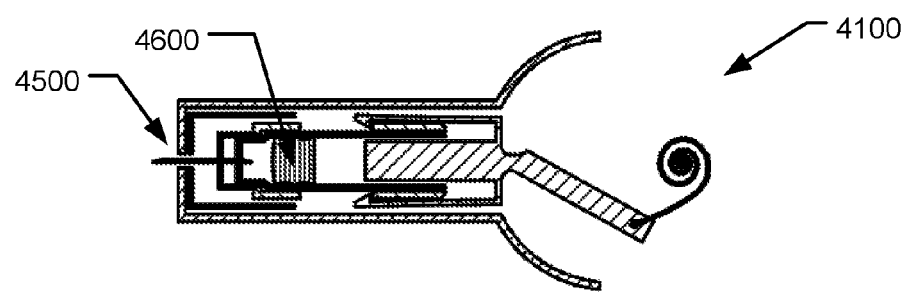
Figure 11E:
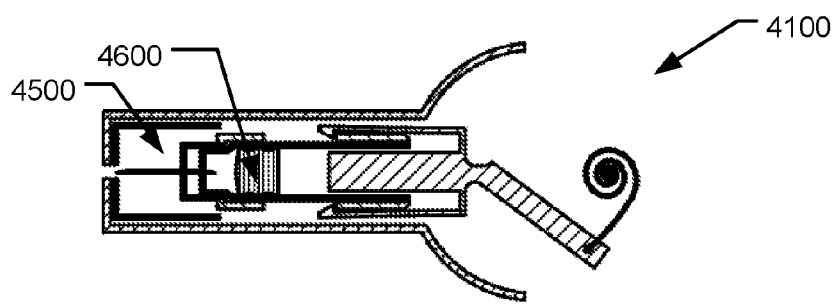
Figure 12:
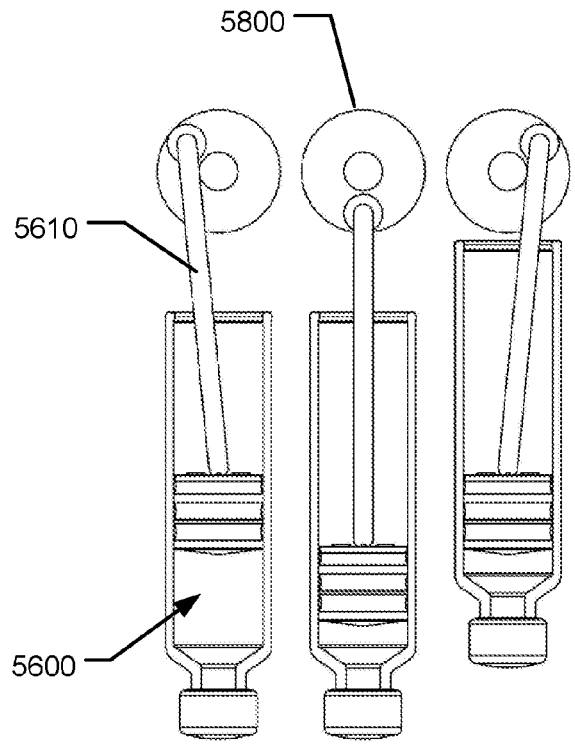

The invention will now be described in further detail with reference to the drawings in which:

FIG. 1a shows a front sectional view of a first embodiment of an injection device 100 according to the first aspect of the invention, in an initial storage state wherein a needle cannula of the device is in a shielded state, FIG. 1b shows a front sectional view of the first embodiment in a state wherein an activator button has been turned for unlocking the activator button, FIG. 1c shows a front sectional view of the first embodiment in a state wherein the activator button has been depressed, FIG. 1d shows a front sectional view of the first embodiment in a state wherein a needle cannula fully protrudes from a needle shielding portion, FIG. 1e shows a front sectional view of the first embodiment in a state wherein a cartridge has been moved relative to the needle cannula for establishing fluid communication, FIG. 1f shows a front sectional view of the first embodiment in an end of stroke condition for a piston of the cartridge at the initial state of a damper, FIG. 1g shows a front sectional view of the first embodiment in a state where the damper has initiated the triggering of a shielding driver, FIG. 1h shows a front sectional view of the first embodiment in a state where the shielding driver has returned the needle cannula into the shielded state, FIG. 2, left part shows a detailed sectional view of the activator button of FIG. 1b and FIG. 2, right part shows a detailed sectional side view of the same, FIG. 3 show a detailed view of a needle assembly according to a second embodiment of the invention, FIG. 4a shows a detailed front sectional view of the damper of the first embodiment in the state as shown in FIG. 1f, FIG. 4b shows a detailed front sectional view of the damper of the first embodiment in the state as shown in FIG. 1g, FIG. 5a through 5h show cross-sectional views of a third embodiment of an injection device in various different states during an injection process, FIG. 6a through 6j show schematic cross-sectional views of a fourth embodiment of an injection device in various different states during an injection process, the device including a damper configuration, FIG. 7a through 7d show schematic representations of a fifth embodiment of an auto-injector in various different states during an injection process, the auto-injector operating according to the first and/or the third aspect of the invention, FIG. 8a through 8m show different views of a sixth embodiment of an auto-injector in various different states A-I during an injection process, the device including a damper configuration, FIG. 9a through 9d show schematic representations of a seventh embodiment of an auto-injector in various different states during an injection process, the auto-injector operating according to the third aspect of the invention, FIG. 10a through 10d show schematic representations of an eight embodiment of an auto-injector in various different states during an injection process, the auto-injector operating according to the third aspect of the invention, FIG. 11a through 11e show schematic representations of a ninth embodiment of an auto-injector in various different states during an injection process, the auto-injector operating according to the third aspect of the invention, FIG. 12 shows a schematic representation of a tenth embodiment of an auto-injector which operates according to the third aspect of the invention, and FIG. 13a-13b, 14a-14b, 15a-15d and 16a-16c show needle assembly details and details relating to a process of bulk sterilization of needle assemblies of the type corresponding to the needle assembly shown in FIG. 3.

FIG. 1a shows a front sectional view of a first embodiment of a medical injection device 100 for medically injecting a pre-determined amount of a liquid medicament. FIG. 1a shows the injection device in a storage condition. The depicted embodiment shows a disposable device which is adapted to administer a fixed dose upon activation for subsequent disposal. The embodiment shows an injection device in the form of an auto-injector which provides automatic needle penetration, automatic injection of medicament and automatic needle retraction. Injection device 100 includes a generally tubular housing 200 having a distal end adapted to be held against an injection site. The distal end of the housing 200 accommodates a needle assembly 500 and defines a needle shielding portion 250 for shielding against unintentional needle sticks before and after an administration. In the shown embodiment, the distal face of needle shielding portion 250 includes a centrally located aperture having a piercable sealing member 255 arranged to normally cover the aperture but allow for a front needle cannula of the needle assembly 500 to protrude a distance from the needle shielding portion 250. At the proximal end of the housing 200 an activation button 300 is arranged. Activation button 300 is movable from an extended position into a depressed position for activating an injection sequence.

Before activation can be carried out by activating activation button 300, it is required that the activation button 300 is turned a quarter turn relative to the condition shown in FIG. 1*a*, i.e. before the activation button 300 can be depressed. The state wherein the activation button 300 has been turned for unlocking the device 100 is shown in FIG. 1*b* and in greater detail in FIG. 2.

The housing 200 of injection device 100 accommodates a medicament filled cartridge 600 having a body 610 defining an outlet 640 at the distal end which is sealed off by a cartridge septum 620 adapted to be pierced by a needle cannula for establishing fluid communication with the cartridge interior. Arranged slideably within body 610 of cartridge 600 is a piston 630. The piston 630 is initially positioned at a predetermined distance from a proximal end face 611 of cartridge body 610. Piston 630 is driveable towards the outlet 640 when a needle pierces the cartridge septum 620 in order to dispense medicament from the cartridge 600. The dispensing is controlled by a dosing mechanism. Cartridge 600 is arranged coaxially with respect to the housing 200 and axially movable within housing 200 from a proximal storage position and into a distal activated position.

Arranged distally in housing 200, needle assembly 500 is mounted coaxially and slideably between a proximal position where a front needle 510 of a needle cannula is in a shielded state and a second distal position where the front needle 510 protrudes through the sealing member 255 i.e. into an unshielded state. In addition, after the needle assembly has been moved to the distal position due to the injection device becoming activated for an administration, the needle assembly may be returned in the proximal direction into its initial proximal position relative to the housing 200. A compression spring forms a shield spring 370 which is located between needle shielding portion 250 and a hub section of needle assembly 500 to urge the needle assembly in the proximal direction, i.e. into its shielded state. During the course of the administering sequence, upon end of dose, the shield spring 370 performs as a shielding driver for actively bringing the injection device from its unshielded state into its shielded state. As shown in FIG. 1*a*, when the injection device 100 is in its storage condition, the needle assembly 500 is arranged in an initially separated configuration with respect to cartridge 600. In the shown embodiment, needle assembly 500 includes a needle cannula having a front needle 510 and a rear needle (not visible) respectively protruding in the distal and proximal directions from a needle hub. Both front needle 510 and rear needle include pointed tips for respectively piercing the skin of a user and the cartridge septum 620. For details of appropriate needle assemblies, reference is made to the discussion below in relation to FIG. 3.

The dosing mechanism is placed in the proximal part of the housing 200 of the device. In the shown embodiment the dosing mechanism comprises piston driver 310 (referred to previously) and an actuator comprising an actuator thrust member 330 and a stored energy source in the form of a pre-stressed compression spring 360. Upon activation, spring 360 is capable of being released to drive forward the actuator thrust member 330 and hence drive forward the piston driver 310.

Axial movement of actuator thrust member 330 is transferred to axial movement of the piston driver 310 as the actuator is released. In the shown embodiment, a damping mechanism is provided between the actuator thrust member 330 and the piston driver 310 and hence, in the shown embodiment, an actuator connector 320 couples the actuator thrust member 330 with piston driver 310.

Upon activation, the injection force being exerted by the stored energy source 360 of the actuator is larger than the force exerted from shield spring 370. In this way, when the stored energy source 360 is released for performing an injection, the stored energy source 360 drives forward the cartridge 600 and the needle assembly 500 thereby overcoming the biasing force of the shield spring 370.

In the shown embodiment, the cartridge 600 is held by means of guiding surfaces of the housing 200 and in the axial direction by means of a piston driver 310 which is attached to the piston 630 of cartridge 600. The attachment may be accomplished by means of a threaded connection, by means of a snap lock or bayonet lock etc. Still, in alternative embodiments, the piston driver 310 may be formed as a unitary component with the cartridge piston 630. Upon activation, in the initial part of the administration sequence, as the piston driver 310 moves within the injector, the cartridge 600 is moved distally as it is not affected by other parts.

In the depicted embodiment, upon activation of the device, the cartridge 600 moves forward and frictionally engages a hub section of the needle assembly 500 which pushes the needle assembly 500 distally until the front needle 510 protrudes a pre-determined distance from the distal face of needle shielding portion 250. Subsequent to this, the cartridge 600 continues its forward movement resulting in the rear needle of needle assembly 500 to pierce the cartridge septum 620 for establishing fluid communication with the cartridge contents. When the cartridge 600 is fully pushed in relative to needle assembly 500 it is stopped, after which the piston 630 begins moving inside the cartridge 600 for the expelling stroke. In alternative embodiments, the device may be configured to first establish fluid communication between the cartridge and the needle cannula before the needle assembly is moved distally to its unshielded state.

In the proximal end of cartridge 600, a bushing member 340 is inserted. Bushing member includes an enlarged rim section 341 adapted to abut against the proximal end face 611 of cartridge 600. Bushing member 340 has an internal bore which is adapted to receive piston driver 310 in a sliding relationship. A distal region 345 of the internal bore is enlarged to perform jointly with a channel 315 formed in piston driver as a control valve (to be described below).

Piston driver 310 is formed as a generally tubular member having a proximal enlarged rim section 311. Internally in piston driver 310 a bore 313 is formed for receiving a distal end of actuator connector 320. In the storage condition of injection device 100, the bore of piston driver 310 and the distal face 322 of actuator connector 320 defines a variable volume reservoir 400 which in the initial condition is filled with a highly viscous fluid, such as grease. The above mentioned control valve 345,315 leads away from said variable volume reservoir 400 thereby forming a damper configuration between the actuator connector 320 and the piston driver 310.

Actuator connector 320 has a tubular part which is slideably received in the bore 313 of piston driver 310 and further has an enlarged head 321 which is adapted to cooperate with actuator thrust member 330.

Referring to FIG. 2 which shows detailed views of the activator mechanism of injection device 100, the depicted embodiment of the actuator thrust member 330 includes retaining portions 335 which in the storage condition of the device 100 retains the actuator thrust member 330 relative to mating retaining surfaces (non-referenced) of the housing against the force of the pre-stressed spring 360. Upon depression of activator button 300, mating release surfaces 305 of activator button 300 forces the retaining portions 335 free of the mating retaining surfaces of the housing to set free movement of actuator thrust member 330. Such configuration is generally known in the field of single use auto-injectors. Alternative activator configurations is envisioned within the scope of the present invention, such as activators arranged in the distal end of the device, such as shield activators, or buttons arranged at the distal end or along a side portion of the housing 200.

Actuator thrust member 330 includes a seat for receiving the distal end of compression spring 360. At its distal end, actuator thrust member 330 further includes a set of distally extending resilient arms ending in deflectable head portions 332 to cooperate with enlarged head 321 of actuator connector 320. In the initial stages of the injection, the resilient arms and the deflectable head portions 332 are forced radially inwards by the housing 200 so that the head portions 332 are biased radially outwards. Each of the deflectable head portions 332 is adapted to move radially outwards when the actuator thrust member 330 has travelled fully in the distal direction. This happens when the deflectable head portions 332 aligns axially with recesses 232 formed in housing 200. As the deflectable head portions 332 move radially outwards the engagement between the actuator thrust member 330 and enlarged head 321 of actuator connector 320 is interrupted. Due to this, the cartridge 600 and needle assembly 500 becomes forced proximally in the device due to the spring force of the shield spring 370. In other embodiments, the actuator thrust member 330 may be designed to travel even further after the engagement between the actuator thrust member 330 and enlarged head 321 of actuator connector 320 has been interrupted, as this will not influence the needle retraction procedure.

As mentioned, in the shown embodiment the actuator is provided as a pre-stressed compression spring 360 which thrust forward the piston driver 310 in the distal direction. Alternatively to using a pre-stressed spring which is compressed during manufacture of the device, the device may include a mechanism for compressing the spring as an initial procedure when taking the device into use. Also, the actuator may in other embodiments be formed as a torsion spring which is pre-stressed to exert a torsion force for driving forward a rotational drive of the dosing mechanism. Alternatively, the actuator may be in the form of a compressed medium such as a gas. Still alternatively, the actuator may include a gas generator such as an electro-chemical cell. Also, an alternative embodiment may involve an actuator where the user manually drives forward the piston driver during injection.

As mentioned above, the piston driver 310 is formed with an enlarged rim section 311 performing as a stop surface positioned a predetermined distance from the distal end of piston driver to cooperate with the rim section 341 of the bushing member 340 to thereby define a precise end of stroke position for the piston 630 inside cartridge 600. As the piston 630, during filling of the cartridge 600, may be accurately positioned with respect to the rear end 611 of the cartridge 600, the exact volume of an expelled dose can be accurately controlled by utilizing the stop surfaces 311 hitting the rim section 341 which is accurately positioned with respect to the rear end 611 of cartridge 600.

In the following, while mainly referring to FIGS. 1a through 1h, the operation sequence of the injection device 100 will be described.

Before use, as described above, the activator button 300 is turned relatively to housing 200 for initially unlocking the device. This state is shown in FIG. 1b. Before this action is carried out, attempting to push down the activator button will not result in activation of the device 100. However, after unlocking, when the user grips the device and the distal end of device 100 is pressed against an injection site, the activation button is pressed in for activating the device (see FIG. 1c).

As the device 100 is activated the actuator thrust member 330 is freed from housing 200. Due to the force exerted by compression spring 360 of the actuator the actuator thrust member 330 is moved distally forcing the actuator connector 320, the piston driver 310, cartridge 600 and needle assembly 500 forward until the front needle protrudes from the needle shielding portion 250 (see FIG. 1d). When used for an It is noted that due to the variable volume reservoir 400 is filled with a viscous fluid which is substantially incompressible, and due to the control valve 315,345 being initially in its closed configuration, the piston driver 310 essentially follows movements of the actuator connector 320. In the state shown in FIG. 1d, the rear needle has not yet pierced the cartridge septum 620.

In the state shown in FIG. 1e, the actuator thrust member 330 has moved further distally which result in the further movement of cartridge 600 relatively to needle assembly 500 and thus result in that the rear needle has pierced the cartridge septum 620 to initiate fluid communication with the cartridge interior. In the shown state, the cartridge 600 has been moved fully to its most distal position relative to housing 200.

This establishment of fluid communication between the needle cannula and the cartridge allows the actuator thrust member 330 to drive forward the piston 630 inside cartridge 600 which continues during the entire injection stroke to the end of stroke condition shown in FIG. 1f where the piston driver enlarged rim section 311 abuts the rim section 341 of bushing member 240. At this point, the piston driver 310 is arrested relative to the cartridge 600. However, due to the compression of the fluid and in particular to the compression of the piston a small amount of fluid may still be expelled from the cartridge through the cannula after the piston driver has stopped its movement. Generally, using prior art devices which are intended for high precision injections, the needle should generally be kept inserted in the skin for a prolonged time, such as 6 to 10 seconds, or even longer to allow the system to relax and decompress and allow the remaining small amount to be expelled until the fluid flow from the needle cannula has been substantially stopped.

In the shown embodiment however, at this stage shown in FIG. 1f, the damper mechanism described above initiated to introduce only a slight delay, such as 0.5 seconds, before the needle cannula is actively driven towards its shielded state to withdraw the front needle from the skin. In FIG. 4a a detailed view of the damper mechanism is shown in the state of the device shown in FIG. 1f. In this state, the piston driver 310 has been moved to its stop relative to bushing member 340 and cartridge 600, i.e. the end of stroke position. Before the injection device 100 enters this state, when the piston driver is located proximally to the position shown, the channel 315 is effectively shut of to seal off variable volume reservoir 400 to preserve its volume. However, shortly before the shown position, channel 315 formed in piston driver 310 has axially aligned with the distal region 345 of bushing member 340 where the internal bore is enlarged. This opens up channel 315 to allow the fluid accommodated in variable volume reservoir 400 to escape in a controlled manner. Due to the continued force exerted by the actuator thrust member 330 the movements of actuator connector 320 continues towards the position shown in FIG. 4b as the fluid of variable volume reservoir 400 is reduced. The movement of actuator connector 320 is stopped when the deflectable head portions 332 of actuator thrust member 330 has reached the recesses 232 formed in housing 200 which is shown in FIGS. 4b and 1g. As the deflectable head portions 332 are biased outwardly, the recesses 232 allows the deflectable head portions 332 to move radially outwards. Hereby, the connection between the deflectable head portions 332 and the enlarged head 321 of actuator connector 320 is discontinued.

Referring now to FIG. 1h, as the actuator connector 320 no longer is exerted to the distally directed force of actuator thrust member 330, the shielding spring 370 now drives the needle assembly 500 and the cartridge 600 in the proximal direction relative to housing 200. Also the bushing member 340, the piston driver 310 and the actuator connector 320 is pushed proximal direction. Hereby the needle is quickly withdrawn from the skin of the user and brought into the shielded state securely hidden internally in the needle shielding portion 250. As described above, the sealing member 255 may be provided at the aperture of needle shielding portion 250 to effectively seal off the aperture so that the small portion of fluid which may be expelled from the needle cannula after needle withdrawal is entrapped or otherwise absorbed inside the device.

Due to the early withdrawal of the needle cannula from the skin, as a fraction of the minor amount of fluid expelled from the cartridge after the point in time where the piston driver is arrested is not used for expelling into the patient, the dosing mechanism is configured to compensate for this surplus amount by adding a similar surplus amount during the expelling stroke before needle withdrawal.

To give an example: If the set pre-determined volume to be dispensed is 0.50 ml, the nominal displaced volume of the cartridge is about 0.51 ml. The volume that is 'lost' by the compression of the system is added by the nominal volume in the cartridge. The needle will be retracted very shortly (about 0.5 second) after the piston rod has been performing the length of the dosing distance. A normal dosing speed of an injection is 0.1 ml/sec. A typical injection of 0.5 ml is therefore 5 seconds. When using a conventional injection device, the user shall typically wait 5 seconds (dosing) plus 6 seconds (relaxation), hence in total 11 seconds. Instead, by using the above described device the user shall only keep the needle in the skin for 5 seconds plus about 0.5 seconds for the activation of the automatic retraction, hence in total about 5.5 seconds. This is a major benefit in respect of the comfort of the patient or medical personnel using the injection device.

In the shown embodiment, a damping configuration is used, but can be omitted provided that a well defined dose length, dose speed and dose duration before needle withdrawal is obtained by the mechanism of the injection device. For the above described dosing method, where the rear part of the cartridge is used for accurately defining start and end positions for the piston to thereby precisely determine the effective stroke length, an accurate dispensing system is provided.

Alternatives for the above damping system may also be used for creating a well defined time delay from the end of stroke condition to the needle withdrawal condition, where the effective duration for needle withdrawal is initiated at or close to the end of stroke instant and where the effective duration of needle withdrawal is below 0.5 seconds, alternatively below 1 second, alternatively below 2 seconds, alternatively below 3 seconds, alternatively below 4 seconds or alternatively below 5 seconds.

Such alternatives may be provided by a mechanical engagement between the piston driver and the actuator connector where the mechanical engagement between the piston driver and the actuator is released when the piston driver enters a particular position relative to the cartridge. Such mechanical engagement may be configured in a way generally corresponding to the shown mechanical engagement between the actuator thrust member 330 and actuator connector 320 such as by incorporating one or more flexible arms which are adapted to release when a particular relative position between the piston driver and the cartridge body is reached during the injection stroke.

In a second embodiment of the injection device 100, as shown in FIG. 3, the needle assembly 500 may include front 515 and rear covers 525 forming sterility sheaths for the front needle 510 and rear needle 520 respectively. In the shown embodiment, the front and rear covers are formed as rubber sheaths which are penetrable by the pointed tip of the respective needle segment. When the top portion of each respective cover is forced towards the needle hub 501 the pointed tips of the particular needle section penetrates the cover allowing the needle section in question to be fully or partly exposed outside the needle cover.

The needle cannula may be attached to the hub 501 by gluing, interference fit or similar joining process. The front 515 and rear cover 525 are attached to the hub 501 either by gluing, welding, interference fit, a separate mounting element, or similar. Prior to use the two covers 515, 525 are in their extended positions in which they cover the front 510 and rear needle 520 respectively.

As described above in connection with the first embodiment, the distal movement of the needle assembly 500 brings the front needle 510 through a small aperture 254 in the needle shielding portion 250. As the needle cannula moves relative to the aperture 254 the front cover 515 is preferably held back by the geometry around the opening, thereby allowing the front needle 510 to penetrate the front cover 515 while the needle cover 515 is being compressed between the needle shielding portion 250 and the needle hub 501. Alternatively the front cover 515 could move through the aperture as well. In this case the front cover 515 would be pressed against the patient's skin, thereby being compressed between device 100 and skin. The compression of the front cover 515 can be either in a concertina-like way or be bent sideways, e.g. radially outwards. The front cover 515 may have a specific geometry to ensure that the front cover 515 is always compressed between needle shielding portion 250 and needle hub 501. The aperture 254 in the needle shielding portion 250 could also have a specific geometry for ensuring correct compression of the front cover 515. As the needle assembly reaches a predetermined position the needle assembly 500 will reach a stop. In this position the front needle will be inserted in the patient's skin and the front cover 515 will be compressed.

After the movement of the needle assembly 500 has reached its stop, the cartridge 600 will move distally relative to housing 200 and needle assembly 500. This movement will cause the septum 620 of the cartridge to contact the rear cover 525, thereby compressing this. The compression of the rear cover 525 will cause the rear needle to penetrate through the rear cover 525 and septum 620 of cartridge 600. The compression of the rear cover 525 can be either in a concertina-like way or be bent sideways. The cartridge 600 is further moved until a predetermined position in which the movement is stopped. The compression of the rear cover 525 could act as dampening for the movement of the cartridge 600, thereby reducing the mechanical impact as the cartridge 600 is stopped. In this position the rear cover 525 is compressed between the hub 501 of the needle assembly 500 and the front end of the cartridge 600. The needle cannula is in this position in contact with both the patient's skin and the medicament contained in the cartridge.

When the needle assembly 500 is withdrawn relative to the needle shielding portion 250, the compressive pressure on the front cover 515 is interrupted. As the needle shielding portion 250 no longer holds the front cover 515 in a compressed position the cover will preferably return to its extended position covering the front needle of the cannula.

The front cover may return to its uncompressed shape due to a natural tendency of the cover to return to this shape. In some embodiments the return of the cover to its uncompressed shape could further act as a spring biasing the needle assembly 500 away from the needle shielding portion 250 of housing thereby obviating the need for a separate shielding spring 370. The front cover 515 may have its most distal part attached to the needle shielding portion 250 so that the proximal movement of the needle hub 501 automatically extends the front cover 515. When the front cover 515 returns to its extended position the cover will prevent excess medicament expelled from the cannula to drip out from the device 100.

Alternative embodiments may include a sponge like material arranged in the vicinity of aperture 254 to absorb or block excess medicament expelled from the cannula after it has been withdrawn into the device. An absorbing material may also be at least partly disposed on the distal face of the injector. In still alternative embodiments, the needle cannula is retracted relatively far back into the pen so that the surplus needs to find way through a sort of labyrinth or long distance to get out. Also an internal portion of the device forming the aperture 254 may include one or more surface portions which are provided with a hydrophobic material to thereby prevent excess medicament from escaping the device after needle withdrawal. The geometry of the aperture is preferably matched with the hydrophobic properties of the material and the medicament fluid in question to create an effective blocking functionality. Other alternatives for avoiding drooling from the device may be provided by using the solutions disclosed in references U.S. Pat. No. 5,957,897, U.S. Pat. No. 5,147,303 and US20030114797. In the above embodiments, because the needle is retracted very fast, the amount of surplus that is spilled on the skin is minimal and insignificant.

Now turning to a third embodiment of an injection device 100' of the invention, FIGS. 5a through 5h show cross-sectional views of a device in various states during an injection procedure. On each of the drawing pages 7-10, the left hand image shows a first cross sectional view through a centre axis of the device in a particular state during injection procedure and the right hand images show side cross sectional views orthogonally to the views in the respective left hand images.

The device 100' includes a housing 200' for at least partly accommodating a medicament cartridge 600'. A distal face of the housing defines a portion which is adapted to cooperate with a needle assembly 500' such as by forming needle holding means 254'. The needle holding means 254' may be adapted to form a needle mounting portion adapted for the attachment of a standard needle assembly, such as by a threaded connection or a bayonet connection. The needle assembly 500' includes front and rear needle parts 510', 520' for respectively piercing the skin of a patient and for piercing a septum of the cartridge 600'.

In alternative embodiments the needle assembly 500' may be generally formed similar to the needle assemblies 500 of the first and second embodiment, i.e. wherein an aperture may be formed in the housing and through which a front needle of the associated needle assembly 500' may be adapted to protrude. In such configuration the needle assembly may be arranged and stored in an interior portion of the housing. Upon activation of such device, the rear needle may be forced to pierce a septum of the cartridge and the front needle may be forced to be exposed outside the housing.

Figure 5A:
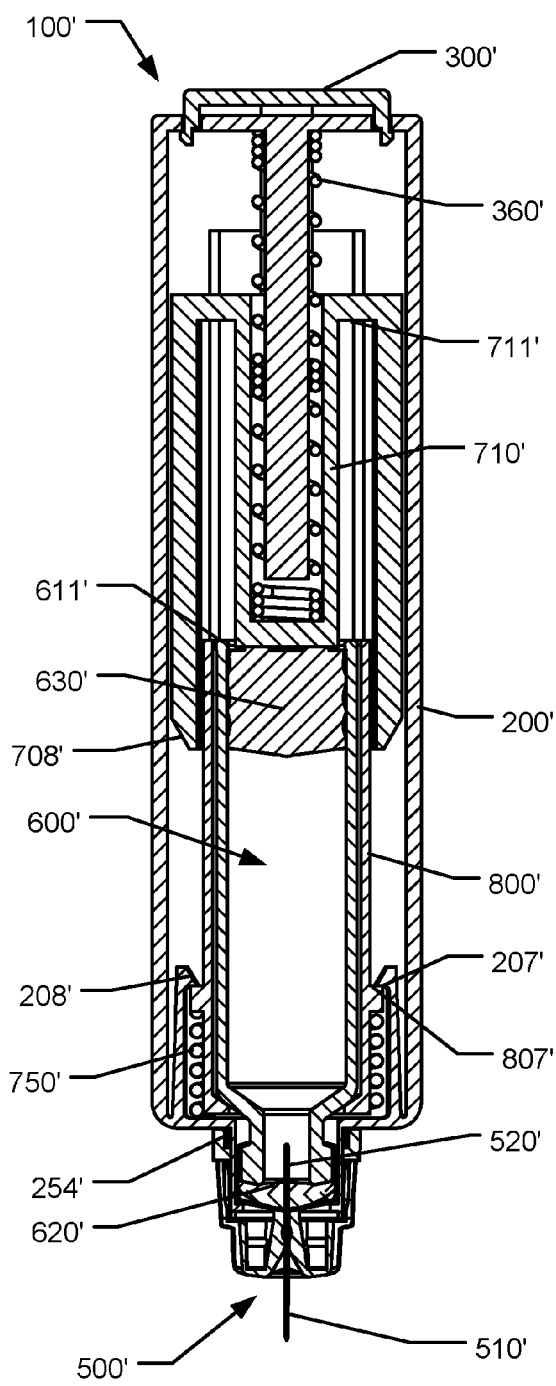
Figure 5B:
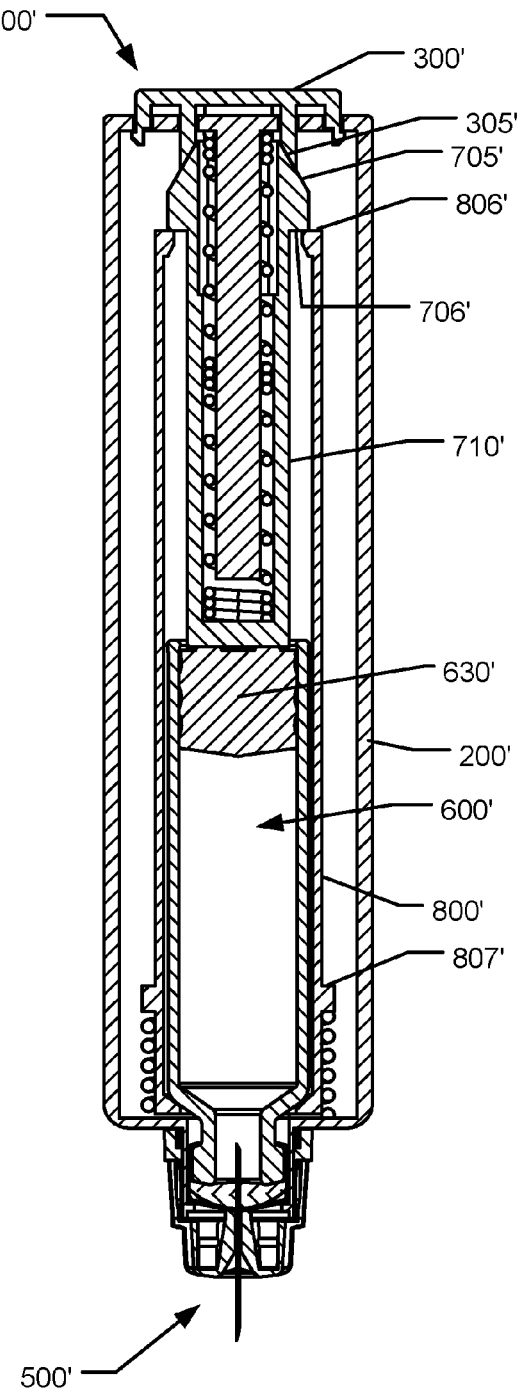
Figure 5C:
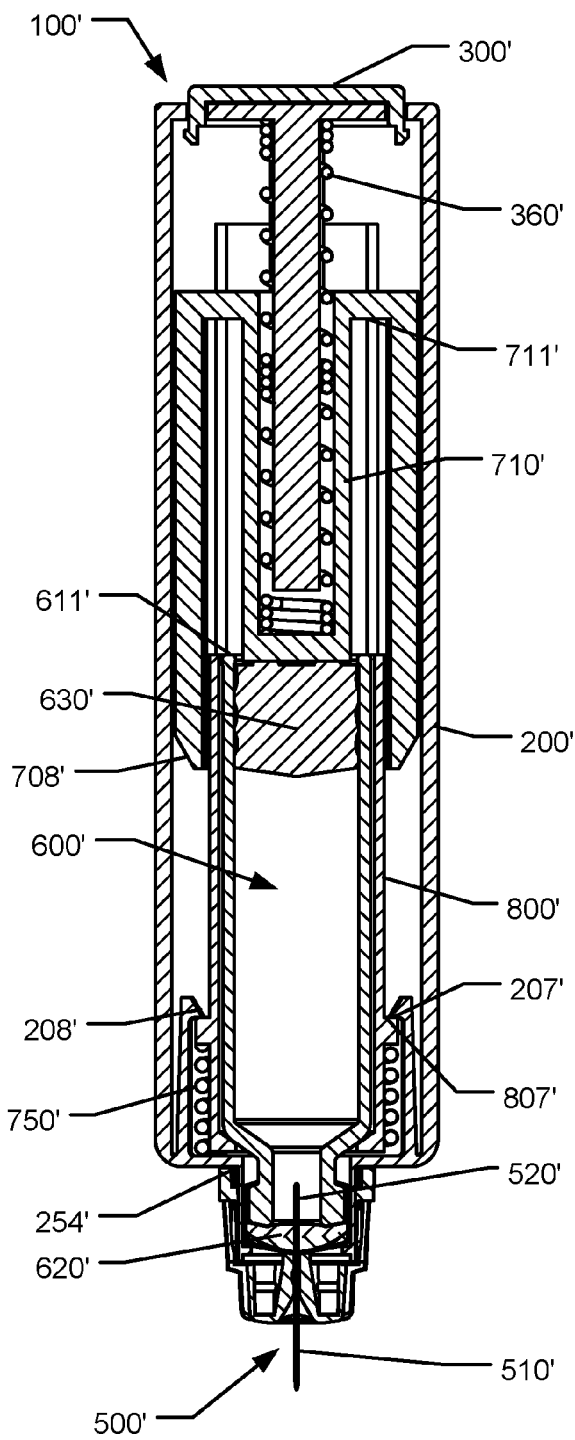
Figure 5D:
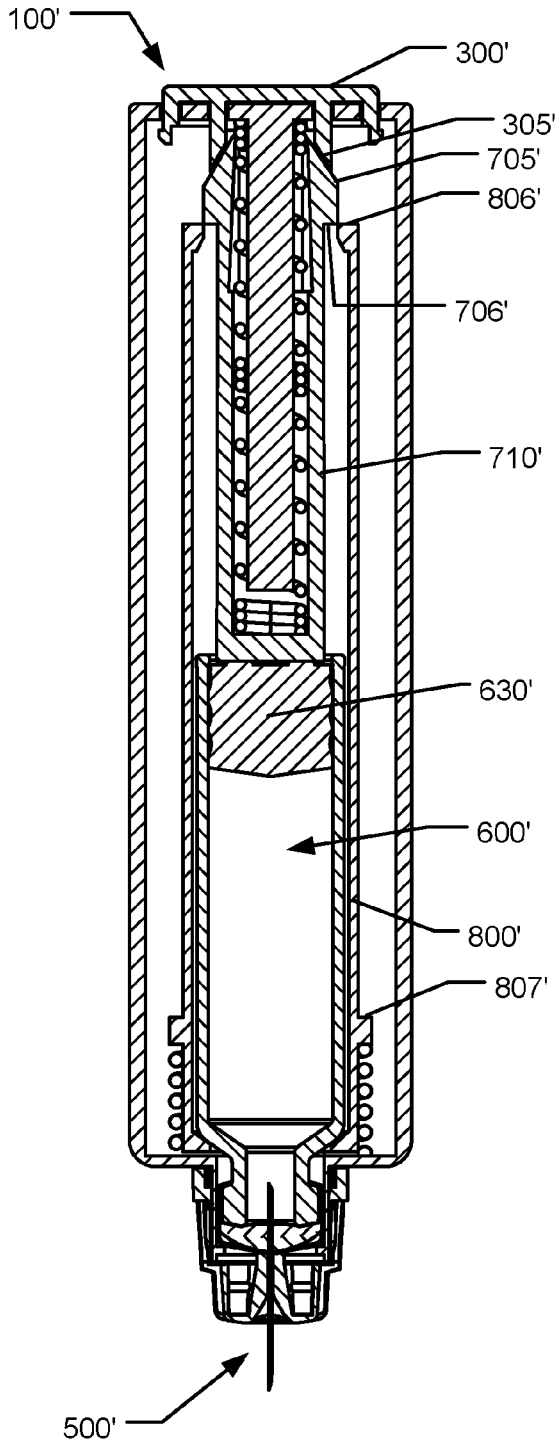
Figure 5E:
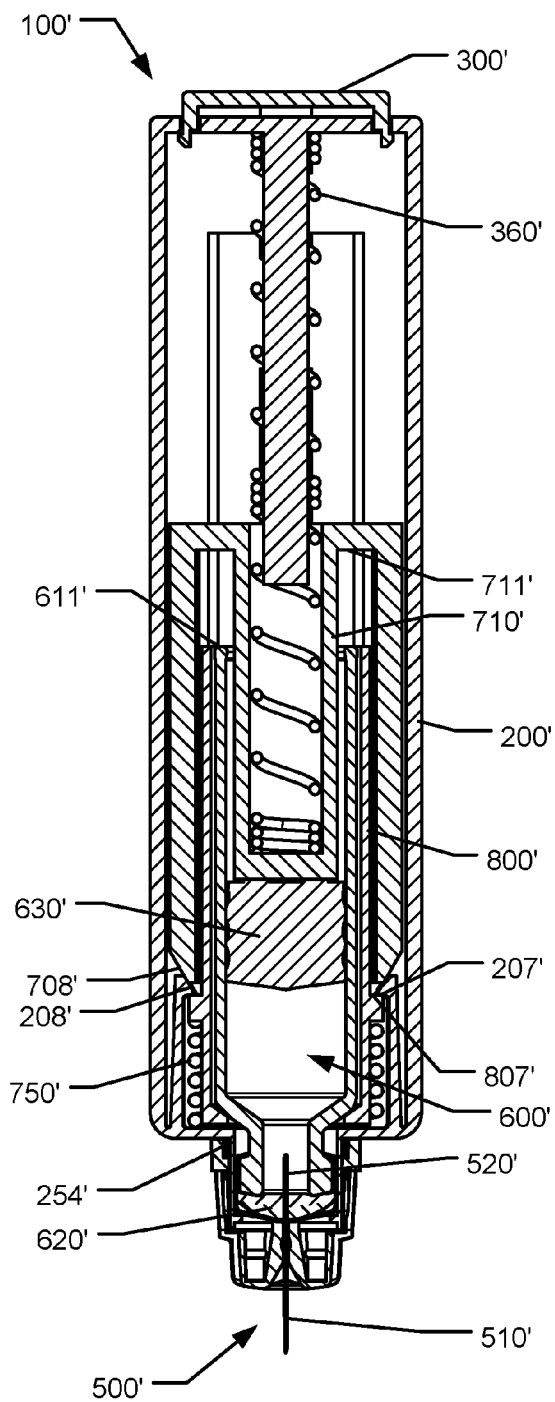
Figure 5F:
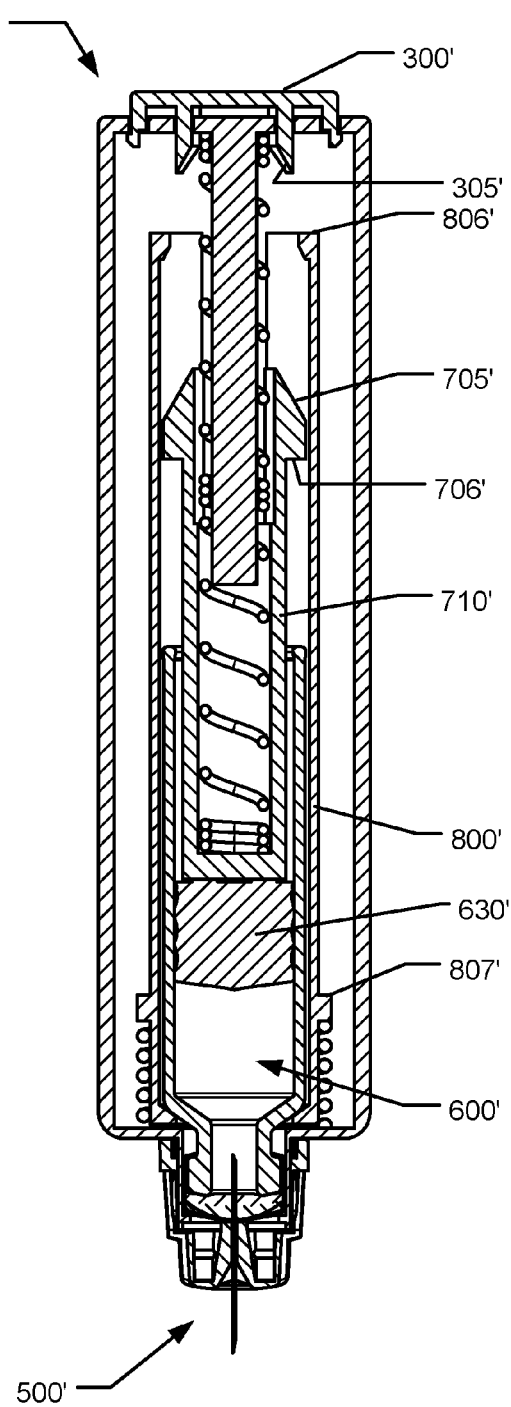
Figures 5G, 5H:
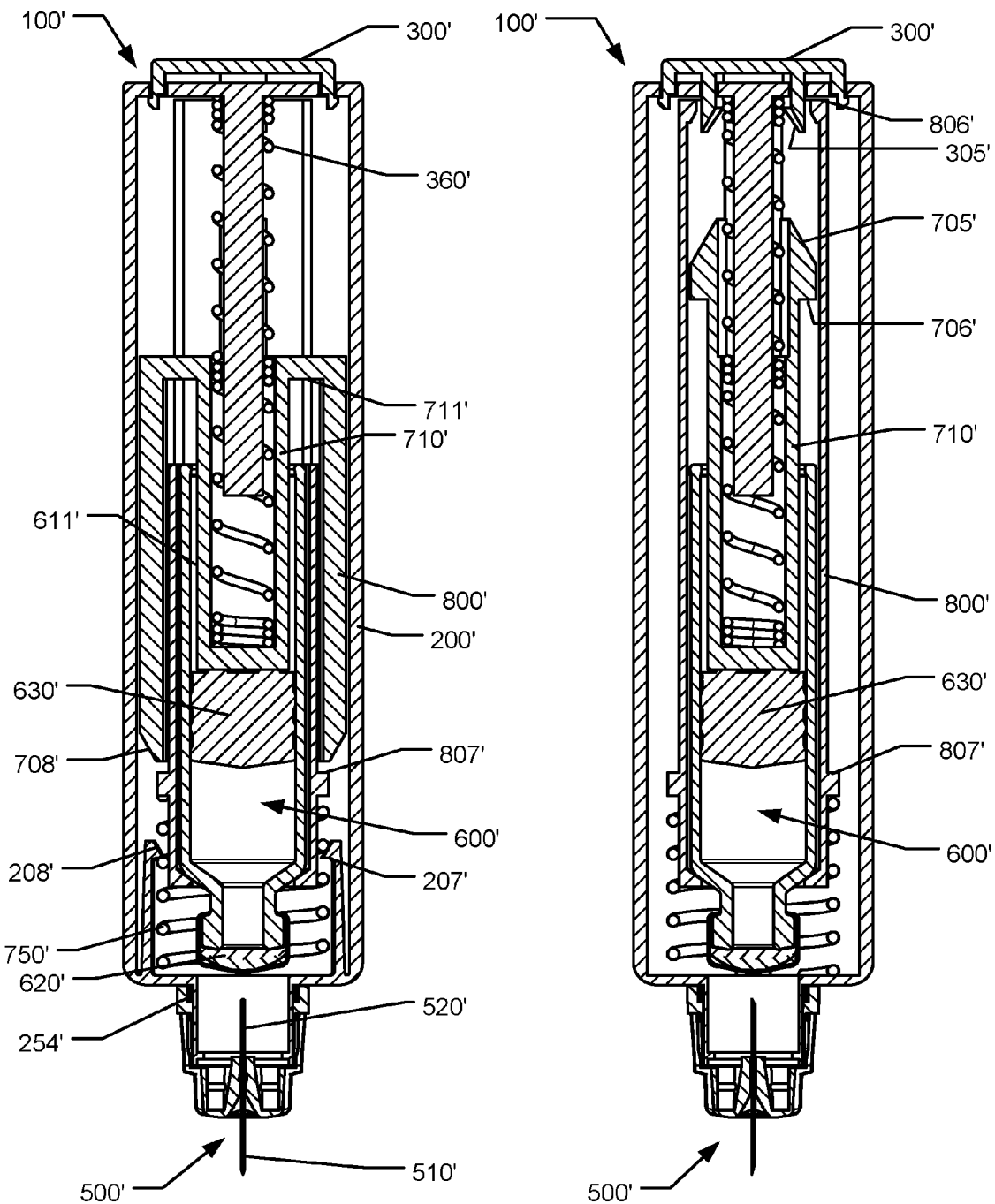

In device 100', the cartridge 600' and the needle assembly 500' are arranged movable with respect to each other, at least for moving the cartridge 600' and the needle assembly 500' from a state where fluid communication is established between cartridge 600' and needle cannula (see FIGS. 5a and 5b) into a state where said fluid communication is interrupted (see FIGS. 5g and 5h).

In the shown embodiment which is intended for manually mounting of a needle assembly prior to an injection procedure, cartridge 600' is held within the device 100' in the distal part of the housing 200' by means of a slideable cartridge holder 800'. A driving or biasing means, such as a cartridge holder spring 750', is arranged between housing 200' and cartridge holder 800' to urge the cartridge holder 800' in the proximal direction. In the state shown in FIG. 5a, by means of a retainer mechanism 207', 807', the cartridge holder 800' is releasably retained in its most distal position where fluid communication is established between cartridge 600' and the needle cannula.

A piston driver 710' is coupled to the piston 630' of cartridge 600' for driving the piston 630' to dispense a predetermined amount of medicament from the cartridge 600'. During the initial sequences of operation, the piston driver 710' is urged in the distal direction due to an actuator in the form of a pre-stressed compression spring 360'. Alternative types of actuators may be provided as mentioned in connection with the discussion of the first embodiment. Also, alternative embodiments may involve an actuator where the user manually drives forward the piston driver during injection. In the shown embodiment, the compression spring 360' is arranged between a proximal part of the housing 200' and a proximal facing surface of the second part 720' of the piston driver in a manner that extends in a bore formed in the second part 720'. In the shown embodiment, the proximal part of the compression spring 360' is guided by means of a stationary guide member (non-referenced) that protrudes from the housing 200' and into the spring 360'.

An activation button 300' is disposed in the proximal end of the device. The activation button 300' includes activation arms each having an inclined surface 305' which engages mating triggering surfaces 705' arranged at the proximal end of the piston driver 710'. When the activation button 300' is pressed down (see FIGS. 5c and 5d) the inclined surfaces 305' will move the triggering surfaces 705' radially inwards. When the triggering surfaces 705' are forced radially inwards, retaining ledges 706' of the piston driver 710' are released from the retaining surfaces 806' of the cartridge holder 800'. Hence, as the spring 360' forces the piston driver 710' distally, the piston 630' of the cartridge 600' moves distally. This movement is maintained until the end of stroke state shown in FIGS. 5e and 5f.

In some embodiments, as discussed below in connection with the fourth embodiment, the end of stroke state is defined when a stop surface 711' of the piston driver 710' abuts the rear face 611' of the cartridge. However, in the depicted embodiment a different configuration completes the expelling operation as will be described below.

Piston driver 710' includes features which cooperate with the retainer mechanism 207', 807' adapted to releasably retain the cartridge 600' and the needle assembly 500' in the state where the cartridge septum 620' is pierced by the rear needle 520'. The retainer includes cooperating features on the cartridge holder 800' and housing 200' respectively. The shown retainer includes activation arms associated with the housing 200' each having an inclined surface 208' which engages mating triggering surfaces 708' arranged in the distal end of the piston driver 710'.

When the piston driver 710' has reached the end of stroke position (see FIGS. 5e and 5f), the triggering surfaces 708' will move the inclined surfaces 208' associated with the housing 200' radially outwards. When the inclined surfaces 208' are forced radially outwards, retaining ledges 807' of the cartridge holder 800' are released from the retaining surfaces 207' of the housing 200'. Hence, as the cartridge holder spring 750' forces the cartridge holder 800' proximally, the cartridge 600' moves quickly away from needle assembly 500'. This state of the device 100' is shown in FIGS. 5g and 5h. It is to be noted that the cartridge holder spring 750' provides sufficient force to overcome the force of the actuator 360'. This movement result in the cartridge septum 620' being resealed due to the tip of the rear needle 520' being either embedded in the cartridge septum or being completely removed from cartridge septum 620'. Due to the interruption of fluid communication between the cartridge interior and the needle cannula the expelling operation is completed in a well defined way.

FIG. 6a through 6j show similar schematic cross-sectional views of a fourth embodiment which is a variant related to the third embodiment described above but with the following modifications. On each of the drawing pages 11-15 the left hand image shows a first cross sectional view through a centre axis of the device in a particular state during injection procedure and the right hand images show side cross sectional views orthogonally to the views in the respective left hand images.

The device 100' according to the fourth embodiment includes an activation button 300' similar to the first and third embodiments. From the unactivated state shown in FIGS. 6a and 6b to the activated state shown in FIGS. 6c and 6d the button 300' acts to release the piston driver.

Figure 6A:
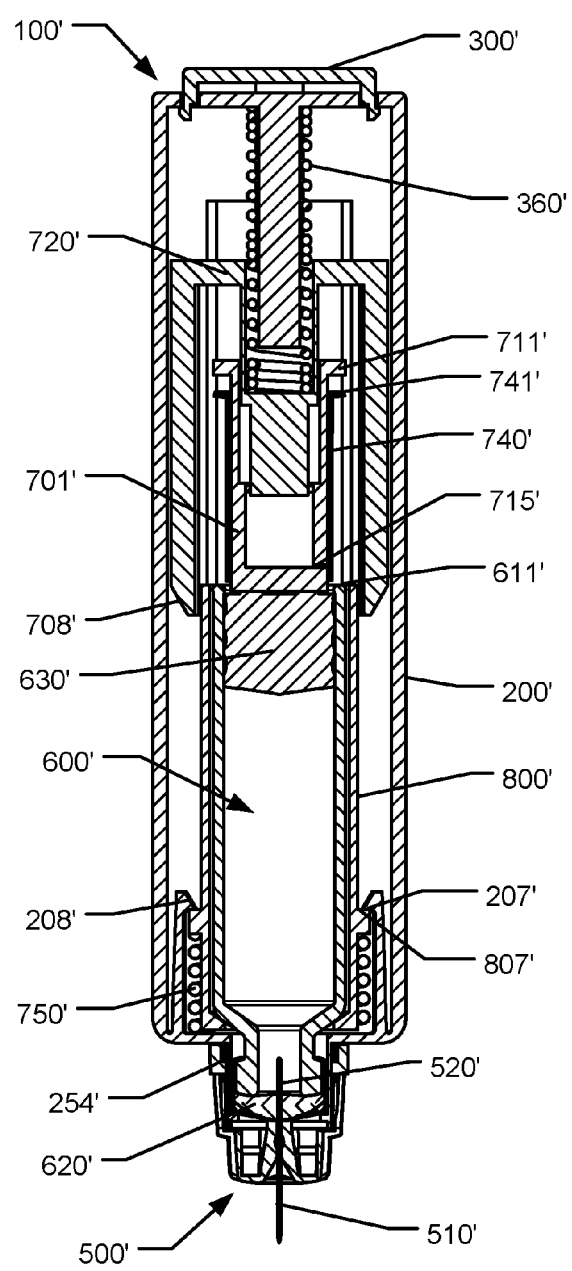
Figure 6B:
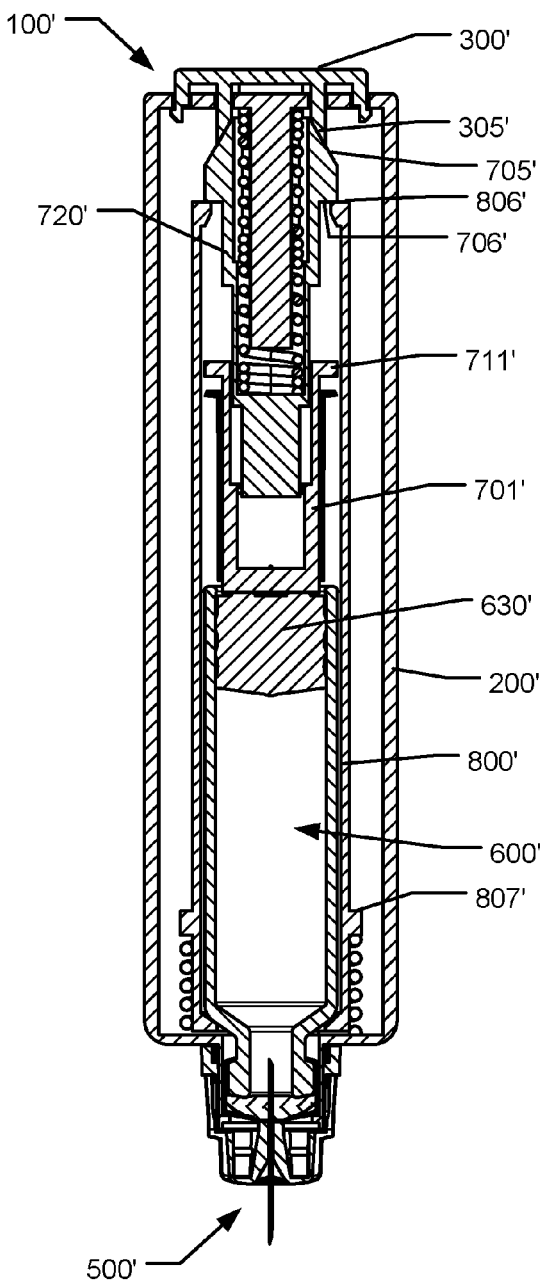
Figures 6E, 6F:
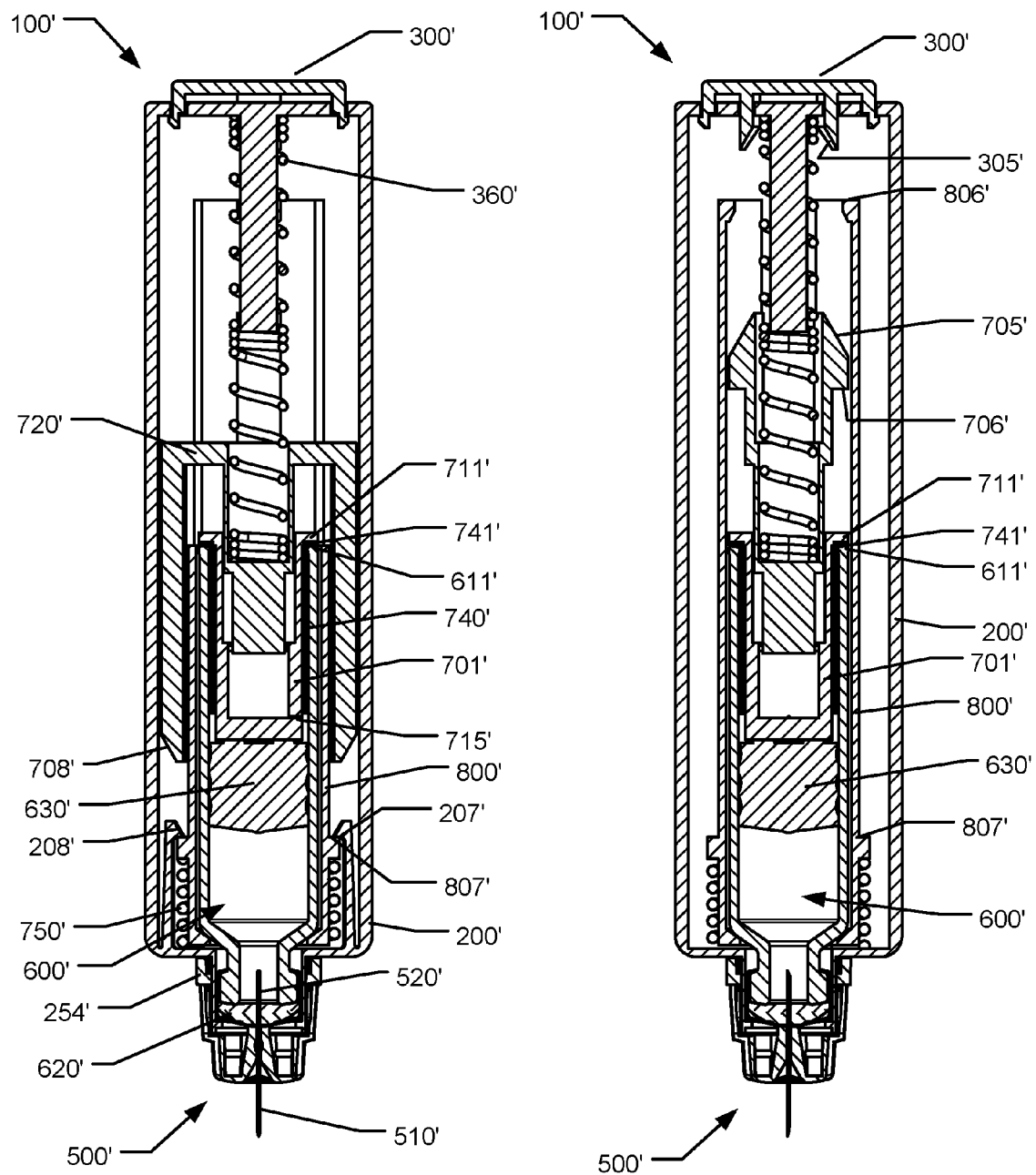
Figures 6G, 6H:
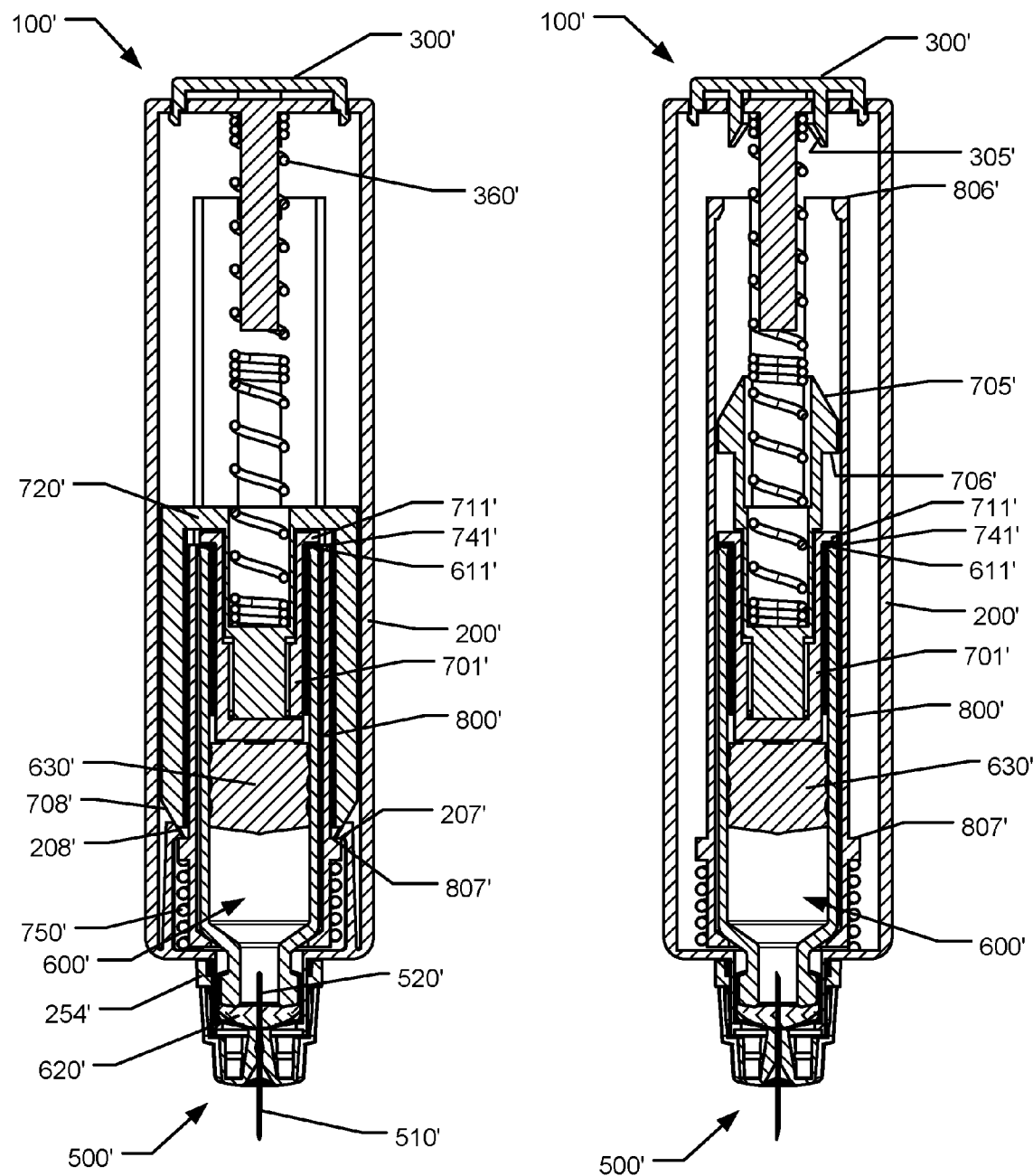
Figures 6I, 6J:
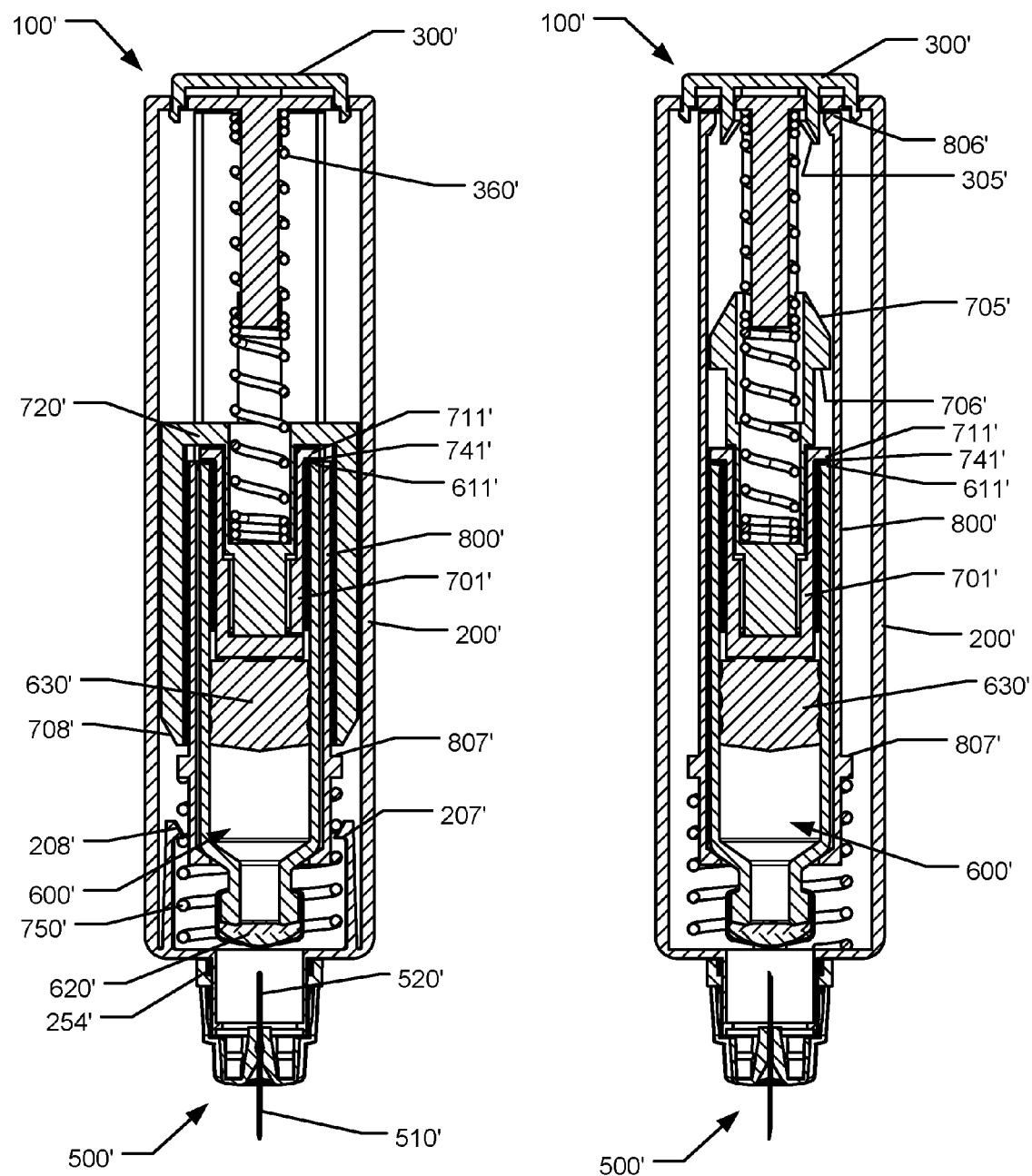

As shown in FIGS. 6a and 6b, the piston driver of the fourth embodiment comprises two main parts, a first part 701' and a second part 720'. The first part 701' and the second part 720' are connected relatively by means of a damper mechanism. The damper mechanism may be configured in a way similar to the damper configuration of the first embodiment, e.g. by forming a variable volume reservoir 400' which is controlled by a control valve. In the depicted embodiment however, the damper mechanism comprises a variant having a bushing member 740' that initially covers a channel 715' formed in the first part 701' and wherein the bushing member 740' is configured to move along with the first part 701' until an extended rim section 741' of bushing member 740' abuts the proximal end face 611' of cartridge 600'. Upon further movement of first part 701' in the distal direction, the first part 701' moves relatively to bushing member 740' to thereby uncover the channel 715', as seen in FIGS. 6e and 6f. This allows for an initially held fluid inside variable volume reservoir 400' to escape and the variable volume reservoir 400' to become compressed while the second part 720' moves further in the distal direction.

The first part 701' of the piston driver is coupled to the piston 630' of the cartridge 600'. As indicated above, the second part 720' is adapted to drive forward the first part 701' during the injection stroke until the first part 701' is arrested relative to the cartridge 600' by the end of stroke limiter arrangement which is provided by parts 611', 741', 711' (see FIGS. 6e and 6f). This stops the movement of the piston 630' inside cartridge 600 so that fluid flow from the cartridge 600' is substantially interrupted. Thereafter, the second part 720' is capable of further movement due to the damper being released for relative movement between the second part 720' and the first part 701' and due to the second part 720' still being exerted to a distally directed force from the actuator 360'. As the second part 720' moves further, the triggering surfaces 708' which is associated with the second part 720' triggers the release of the retainer (see FIGS. 6g and 6h). In the depicted embodiment, this releases the cartridge holder 800' relative to the housing 200'. The cartridge holder spring 750' thus forces the cartridge holder 800' proximally to thereby quickly move the cartridge 600' away from needle assembly 500'. This effectively interrupts the fluid communication between the cartridge interior and the needle cannula (see FIGS. 6i and 6j).

In this way, compared to the third embodiment, a damper configuration such as the one described in accordance with the fourth embodiment may be used in devices where tolerances of the various parts of the device make this inclusion desirable. For example, as the length of the cartridge may be associated with comparatively large tolerance variations, the damper configuration ensures proper cartridge retraction even for cartridges having large variances relative to the nominal cartridge length. Due to the end of stroke limiter being defined by the proximal end face of the cartridge the accuracy of the dosage amount expelled during injection can be ensured with great accuracy if the piston of the cartridge is accurately positioned relative to the proximal end face of the cartridge during the filling stage of the cartridge.

Alternatives for the described damping system may also be used for creating a well defined time delay from the end of stroke condition to the fluid communication interruption condition, where the effective duration of needle withdrawal is below 0.5 seconds, alternatively below 1 second, alternatively below 2 seconds, alternatively below 3 seconds, alternatively below 4 seconds or alternatively below 5 seconds.

As discussed in relation to the first embodiment, the surplus amount of medication that typically is expelled after the end of stroke condition in prior art devices, is taken into account when designing the injectors described herein such that this surplus is delivered during the injection stroke.

The embodiments of the devices 100' shown in FIGS. 5a through 5h, and respectively in FIGS. 6a through 6j may incorporate a relatively thick cartridge septum 620'. Such devices may be configured to interrupt fluid flow when the needle is partly withdrawn with respect to the cartridge septum to provide an effective resealing of the septum and yet be configured to maintain the tip of the rear needle inserted in the septum to effectuate a sealing of the needle cannula so as to avoid back flow from the skin of the patient. A similar effect may be obtained by using a separate sealing member arranged between the cartridge septum and a needle hub of the needle assembly. The rear needle may be adapted to protrude through such separate sealing member during or prior to the injection sequence. However, after the cartridge is retracted from the rear needle, at the end of stroke condition, the tip of the rear needle is embedded into this separate sealing member to effectively block the lumen of the needle cannula.

The devices shown in the third and fourth embodiments may include a mechanism and needle holding means which initially holds the cartridge and the needle assembly as separated components and which, either before activation or in response to activation, mounts the needle onto the cartridge as an initial operating sequence. Alternatively, a standard double pointed needle may manually be mounted onto needle holding means of the device before activation.

Also, the exposed front needle described in connection with the embodiments shown in FIGS. 5a through 5h and in FIGS. 6a through 6j may be moved into a shielded configuration after use of the injector, for example by incorporating a needle shield relative to which the needle is retracted after use, or by incorporating a needle shield which moves relative to the needle to render the needle hidden and inaccessible after use.

Devices using the injection principles shown in the first through fourth embodiments may indicate the end of dose condition (the fluid interruption stage) by generating one or more of an audible signal such as a click sound, a tactile signal, or a visual signal upon completion of the administration. The signal may inherently be generated by the operation of a return spring (if such spring is used) which provides either needle retraction in the device or cartridge retraction from the needle. Alternatively it may be generated by a separate deflection element which emits a signal at the time where the administration is completed.

FIG. 7a through 7d show schematic views of the working principle of a fifth embodiment of an injection device 1100. Injection device 1100 generally operates similar to injection device 100 of the first embodiment but with the following modifications. Reference numbers for the fifth embodiment for like parts and features generally share the same reference numbers as for the first embodiment but has denoted with a "1" digit in front of the reference numbers of the first embodiment, i.e. housing "1200" corresponds to housing "200" and actuator thrust member "1330" corresponds to actuator thrust member "330", etc.

For providing a compact device 1200, the shown embodiment provides the cartridge to be arranged along a first axis and the actuator and driving components to be arranged at a second axis parallel to the first axis and spaced relatively thereto. However, this layout is only optional.

Figure 7A:
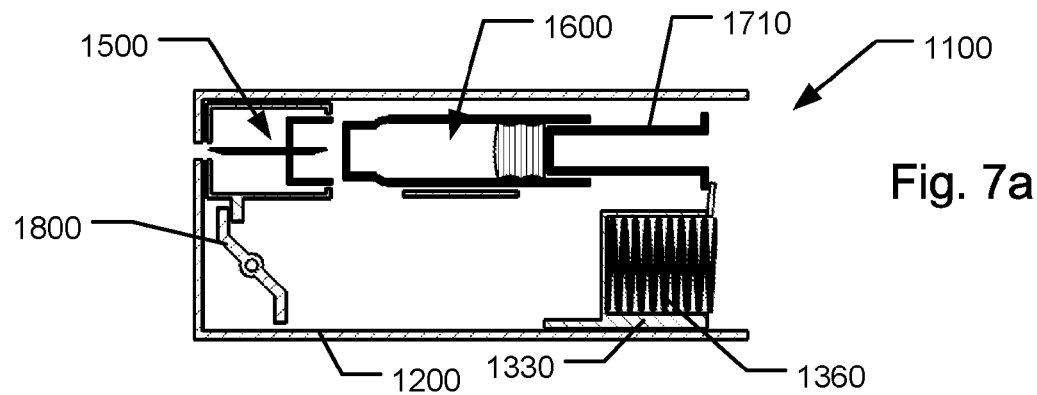

In the device 1100 shown in FIG. 7a, which shows the device in its storage condition before activation, the shield spring 370 of the first embodiment has been omitted and been replaced by another mechanism for performing as a shielding driver 370. In this mechanism, a single actuator compression spring 1360 is used both for driving parts of the injection device in the distal direction and subsequently for driving parts of the injection device in the proximal direction. For this to be accomplished a force transfer mechanism is provided.

Figure 7B:
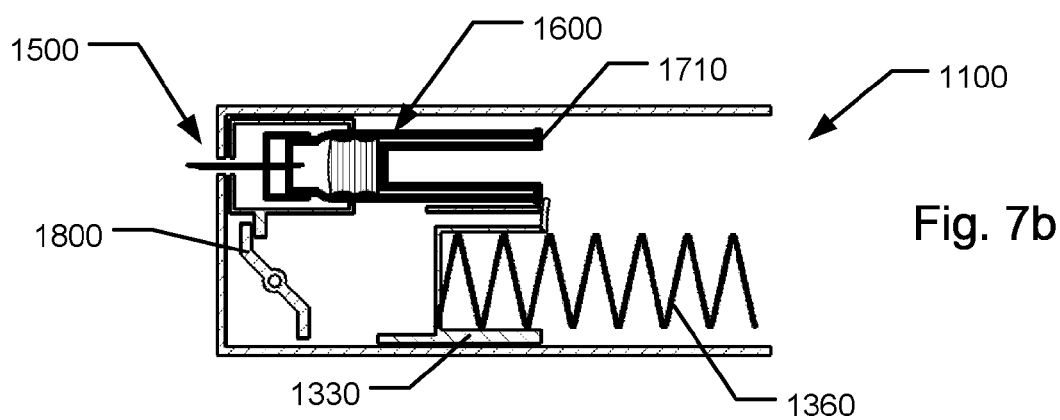

Compression spring 1360 and actuator thrust member 1330 first drives the piston driver 1710 in the distal direction for facilitating the driving of the cartridge 1600 and the needle assembly 1500 distally for shifting the front needle into its unshielded state, then for moving the cartridge 1600 further in the distal direction for insertion of the front needle into the skin of the user and for establishing fluid communication between cartridge 1600 interior and the rear needle cannula of the needle assembly 1500. Lastly, it drives the piston of the cartridge 1600 for expelling the medicament through the needle cannula. This stage is depicted in FIG. 7b. In the shown embodiment, a force transfer mechanism has been introduced with a force transfer member 1800 being able to rotate between two rotational positions. The force transfer member 1800 comprises a first arm for cooperating with the needle assembly 1500 and a second arm for cooperating with a trigger surface 1338 provided on a distally extending arm arranged on actuator thrust member 1330.

Figure 7C:
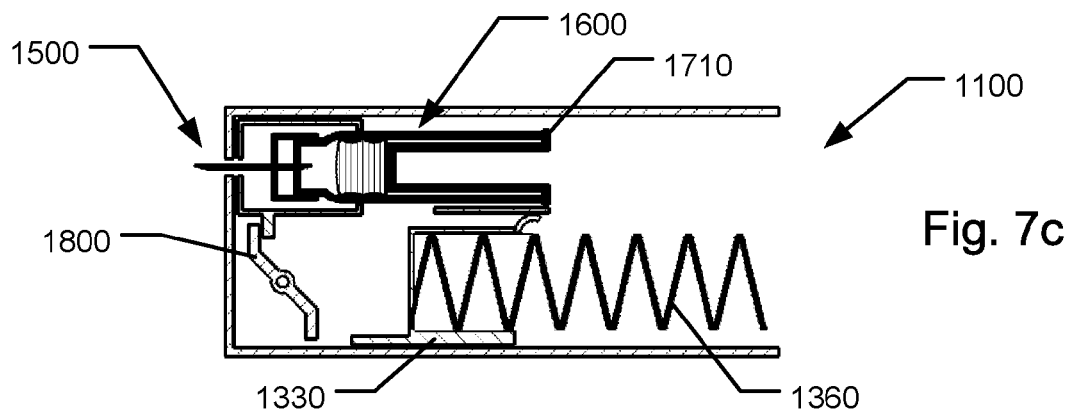

After the full dose has been expelled from cartridge 1600, the actuator thrust member 1330 then decouples from the piston driver 1710 where after it proceeds further in the distal direction towards the force transfer member 1800 (see FIG. 7c).

Figure 7D:
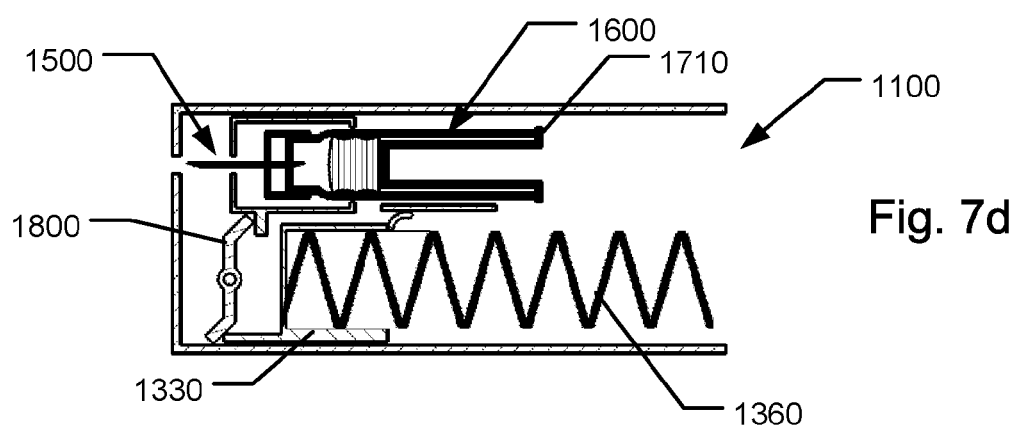

At the stage shown in FIG. 7d, the actuator thrust member 1330 has moved towards its most distal position. Due to the interaction between the actuator thrust member 1330 and the force transfer member 1800, the force transfer member 1800 is moved rotationally clockwise. As the force transfer member 1800 further cooperates with the needle assembly 1500, the clockwise movement of the force transfer member causes the force originating from compression spring 1360 to act on the needle assembly 1500 in a direction opposite to the initial direction of movement of the distal end of compression spring 1360 to thereby withdraw the needle assembly back into the housing 1200 of the device. Hence, the front end of the needle assembly is rendered inaccessible. In a not shown variant the force transfer member may be coupled to the cartridge instead of the needle assembly. In such configuration, the clockwise movement of the force transfer member may be used for separating the cartridge from the needle assembly to thereby interrupt fluid communication between the needle and the cartridge interior in a manner corresponding to that described above in connection with the first, third and fourth embodiments.

It is to be noted that in the schematic representation shown in FIG. 7a-7d, a damping mechanism has been omitted. Instead, a release mechanism is configured so as to release the actuator thrust member from the piston driver when the piston driver enters a specific location during the injection process.

FIGS. 8a through 8m show different views of a detailed version of the fifth embodiment of an injection device 1100, the general working principle closely corresponding to the overall principle described in accordance with FIGS. 7a to 7d.

Again, parts having reference numbers listed in FIGS. 8a-8m generally correspond to similar parts of the first embodiment, but having a "1" digit denoted in front, i.e. part number "1310" corresponds to part number "310" in the first embodiment, etc.

Figure 8A:
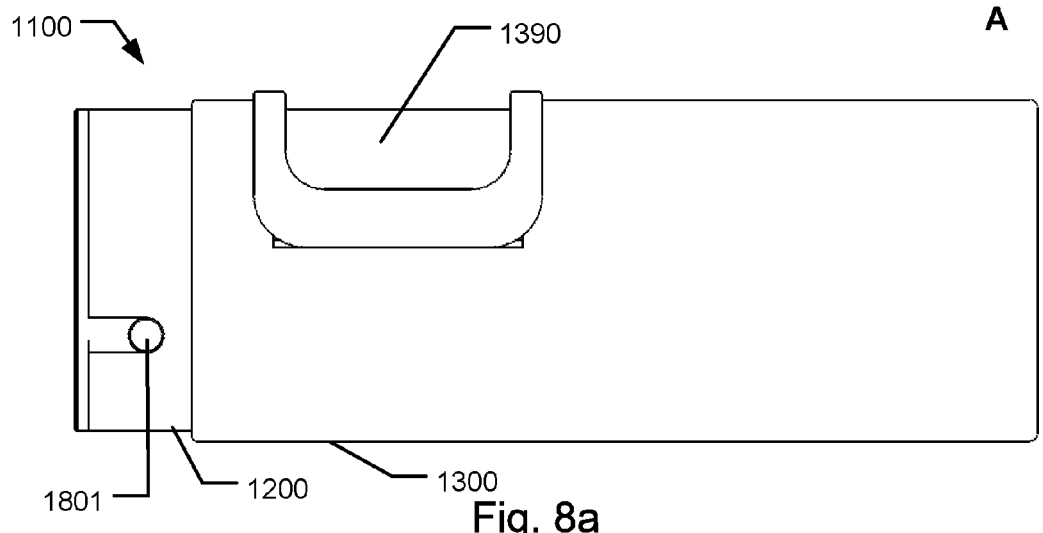

In FIG. 8a an external front view is depicted of the device 1100 having a housing 1200 and an activator 1300 which is provided in the form of a gripping member. The housing 1200 extends from the gripping member (activator 1300) at the distal part thereof, that is the needle end of the device 1100. In the depicted state, designated state "A" in FIGS. 8a, 8b and 8c, a removable lid section 1390 is coupled to activator 1300. In the storage state, an additional cap member (not shown) may be attached to the distal part of activator 1300 to partly or fully encircle the free part of housing 1200 to thereby render the activator 1300 inoperable relative to the housing 1200. In other embodiments such additional cap member and the lid section forms a unitary member. In FIG. 8a a pin 1801 of a force transfer member 1800 arranged internally in the housing 1200 can be viewed.

Figure 8B:
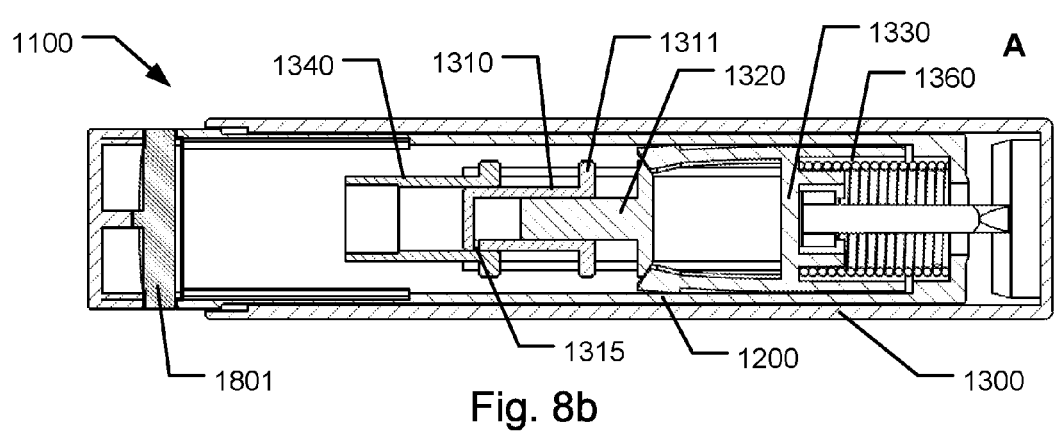

FIG. 8b shows a cross sectional side view of device 1100 in its state "A", the view being normal to the extension of pin 1801 of force transfer member 1800. This view mainly depicts the dosing mechanism of the device 1100 which generally corresponds to the dosing mechanism described in connection with the first embodiment (FIGS. 1a through 1h). Again in this embodiment the dosing mechanism comprises a damping mechanism. The dosing mechanism of the device 1100 basically comprises actuator compression spring 1360 which exerts a distally directed force on actuator thrust member 1330 which again sequentially exerts distal forces on actuator connector 1320/piston driver 1310 and force transfer member 1800.

Figure 8C:
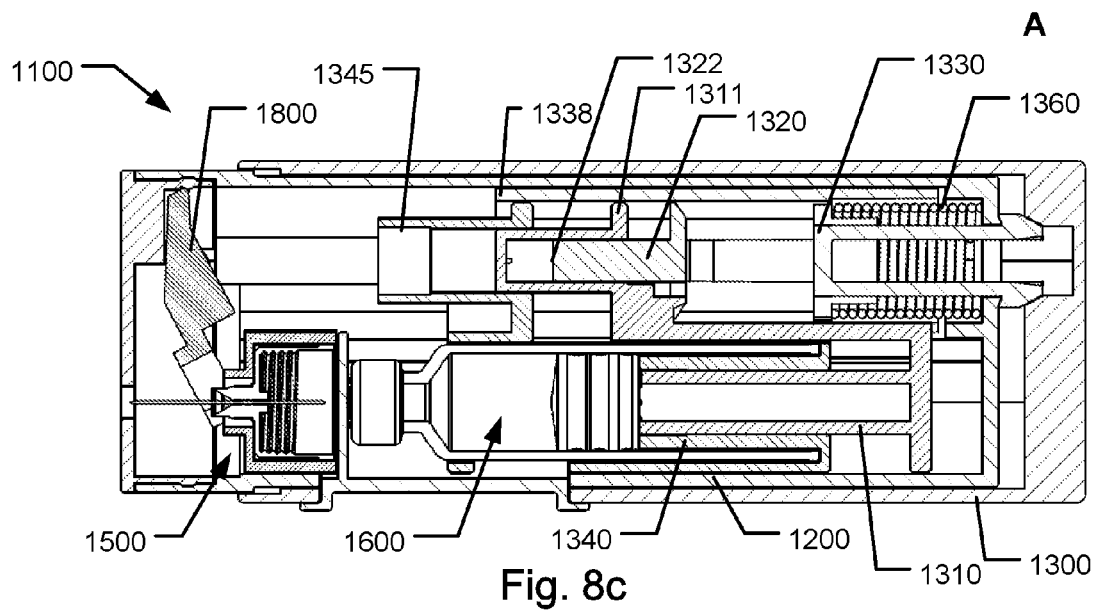

FIG. 8c shows a cross sectional front view through a longitudinal central axis of cartridge 1600 and needle assembly 1500. Also, this cross sectional front view runs through a central longitudinal axis of the dosing mechanism described in connection with FIG. 8b. In the initial state, the needle assembly 1500 and cartridge 1600 are maintained in a separated configuration, i.e. with the septum of cartridge 1600 in a sealing state.

In FIG. 8c it is readily apparent that the piston driver 1310 of the dosing mechanism comprises a part which extends from the longitudinal axis of the damping mechanism and sideways to the longitudinal axis of the cartridge to allow the piston driver 1310 to cooperate with the piston of cartridge 1600. Also bushing member 1340 extends sideways between the said axes. The piston driver 1310 is attached to the piston of cartridge 1600 and as such holds the cartridge 1600 relative to the housing 1200.

Figure 8D:
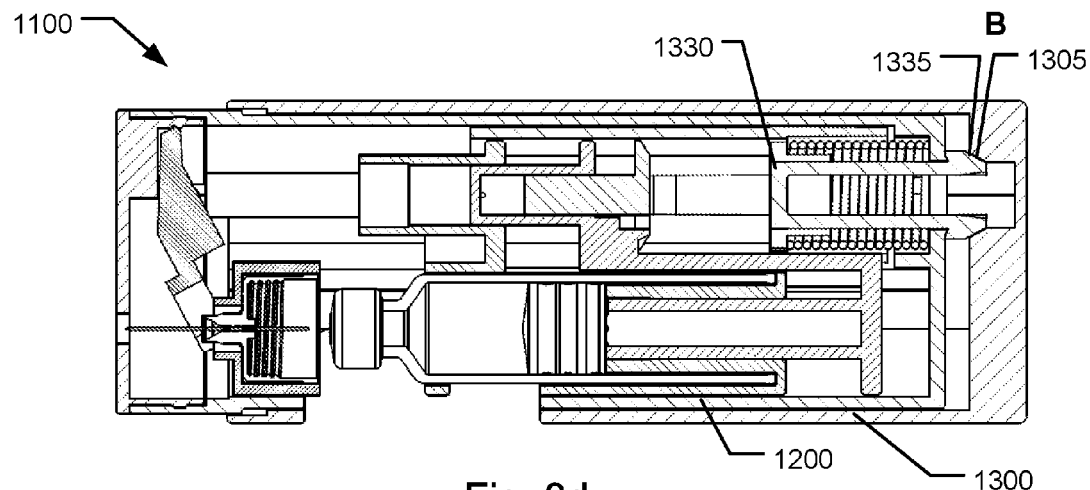
Figure 8E:
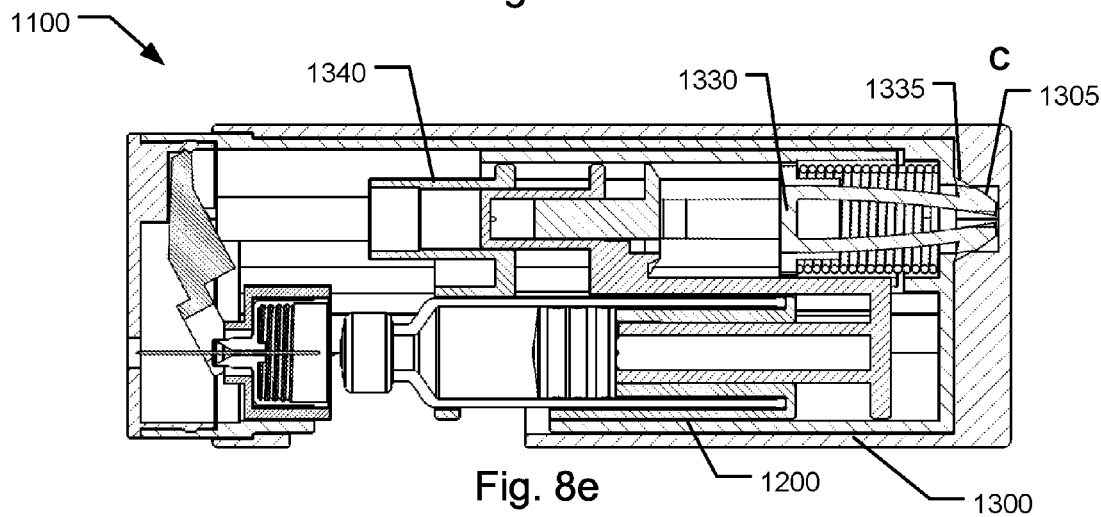
Figure 8F:
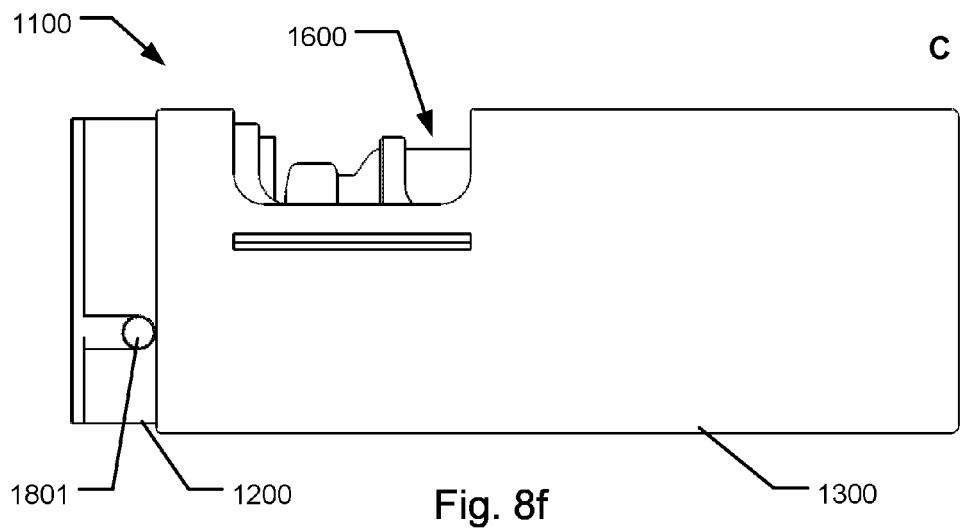
Figure 8G:
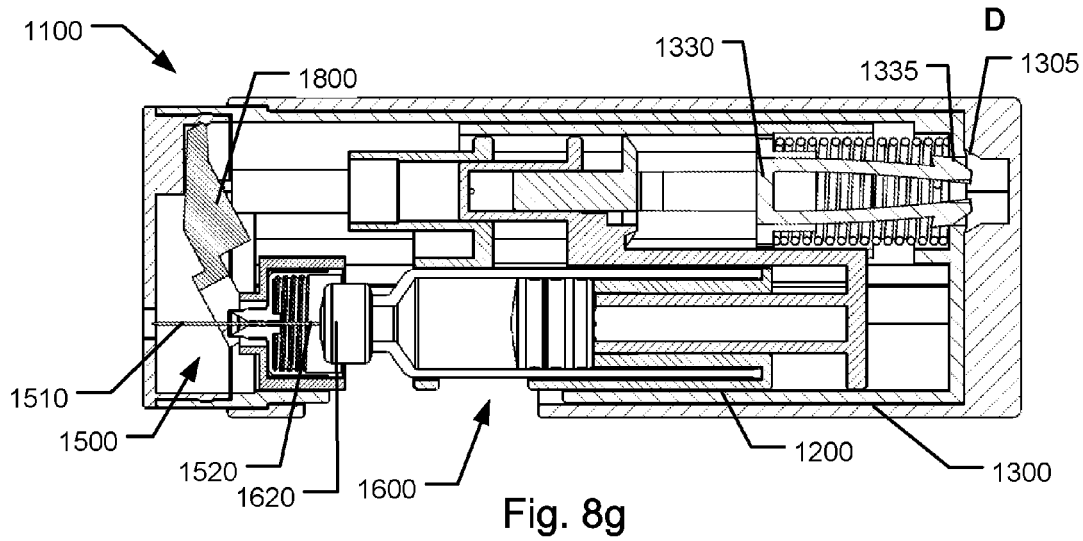
Figure 8H:
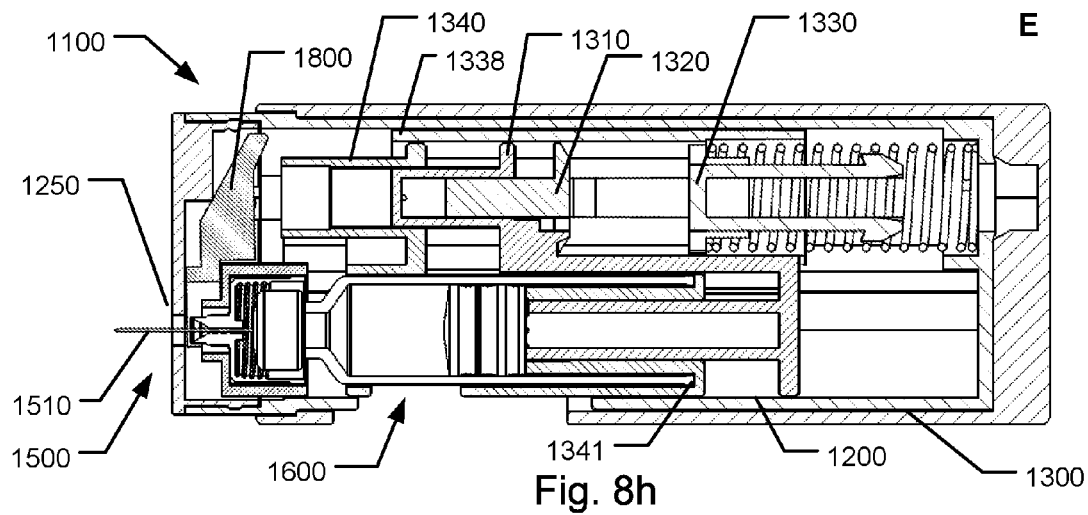
Figure 8I:
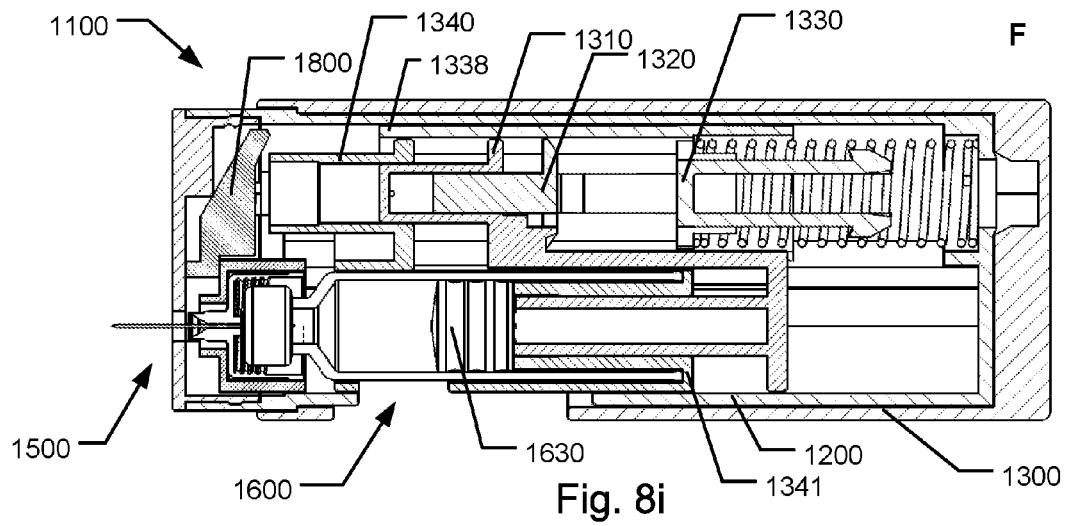

When comparing FIG. 8c with FIG. 8d (showing the device 1100 in state "B"), it becomes apparent that the lid section 1390 has been removed allowing visual inspection of cartridge 1600. It is also apparent that the lid section 1390 initially holds the cartridge 1600 in a separated configuration relative needle assembly 1500 by means of a wall section extending from the lid section 1390. In other embodiments, the removal of lid section 1390 may additionally serve as a means of removing one or more sterility seals from the needle assembly 1500. However, in the shown embodiment, the needle assembly 1500 is only shown schematically omitting features for maintaining the needle assembly sterile prior to use.

In state "A", "B", and "C", the compression spring 1360 is in its initial stage. Upon triggering of the device 1100, by moving the activator 1300 distally relative to the housing 1200 (see state "C", FIGS. 8e and 8f), the spring force of compression spring 1360 is released thereby freeing the actuator thrust member 1330 for subsequent movement in the distal direction. FIG. 8c shows the force transfer member 1800 in a first rotational position, the force transfer member 1330 having a first arm portion for cooperating with the needle assembly 1500 and a second arm portion for cooperating with a trigger surface 1338 of the actuator thrust member 1330. When the needle assembly 1500 is moved distally the force transfer member 1800 is rotated in the clockwise direction to the second rotational position. Later, when the force transfer member 1800 is rotated counter clockwise to the first rotational position, the needle assembly 1500 is moved in the proximal direction relative to the housing 1200, i.e. for the front needle 1510 to enter its shielded state.

As the actuator thrust member 1330 initially is coupled actuator connector 1320 by means of deflectable head portions 1332 (see FIG. 8m, state "B" and "G") the forward movement of actuator thrust member 1330 is directly coupled to the piston driver 1310 so that these two components travel together.

When device 1100 transfers into state "D" (FIG. 8g), the piston driver 1310 has moved the cartridge 1600 distally to initially engage the needle assembly 1500. Due to a frictional engagement, the needle assembly 1500 is moved distally for the front needle 1510 to protrude through an aperture 1250 formed in the distal end face of housing 1200 and simultaneously pushing the force transfer member 1800 in the clockwise direction (state "E"). Subsequently, the cartridge 1600 is moved even further distally for the rear needle 1520 to pierce septum 1620 of cartridge 1600 (see state "F", FIG. 8i) whereby the cartridge is locked against further distal movements. Also bushing member 1340 is halted to prevent further distal movement relative to the housing 1200.

Figure 8J:
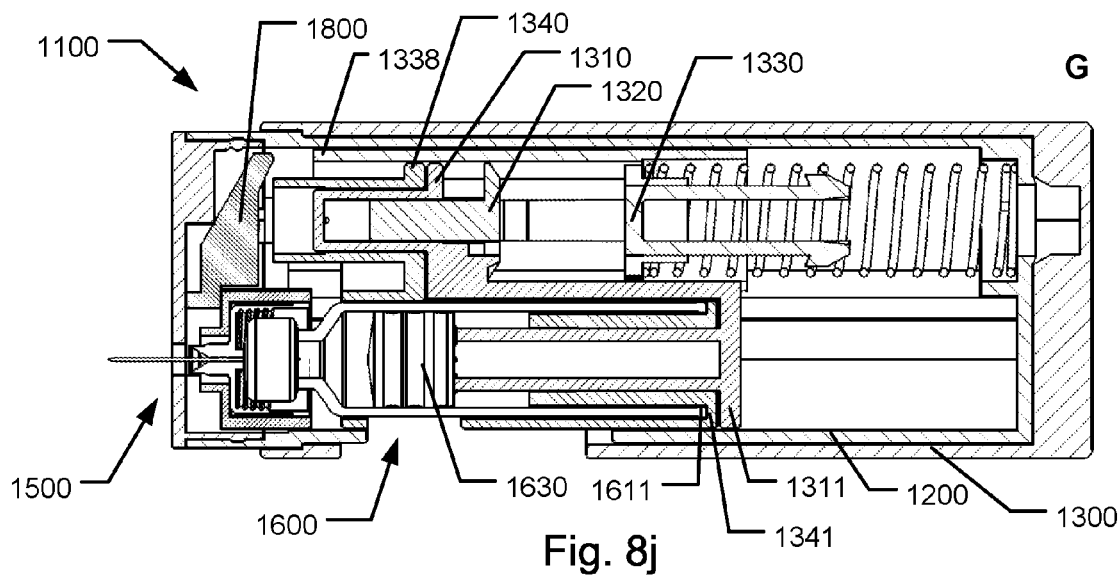
Figure 8K:
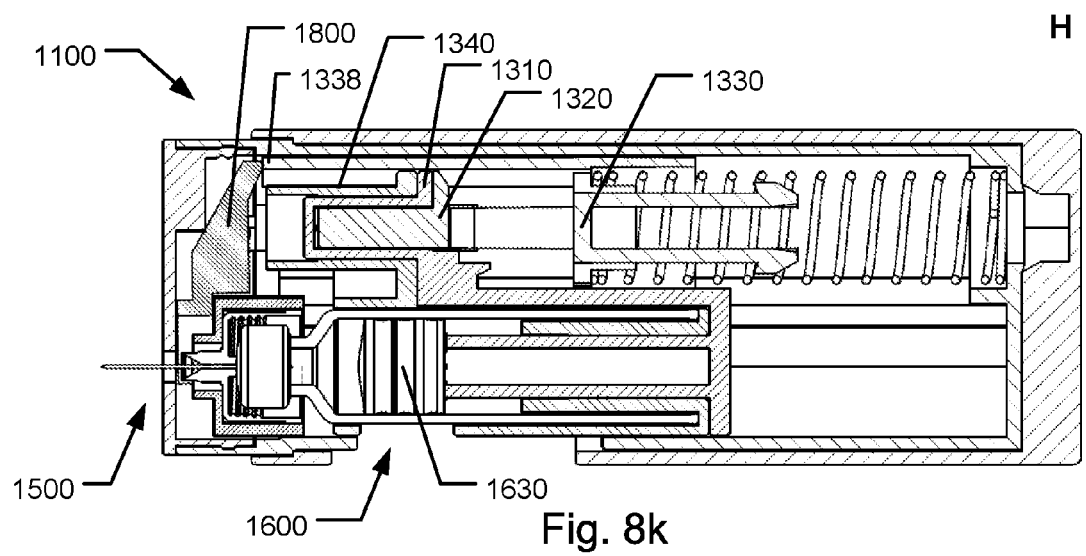
Figure 8L:
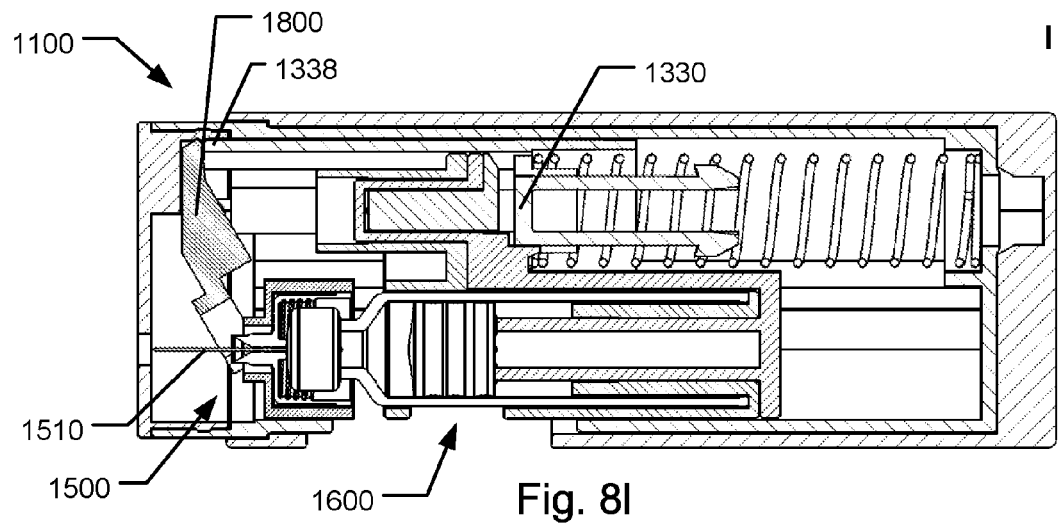
Figure 8M:
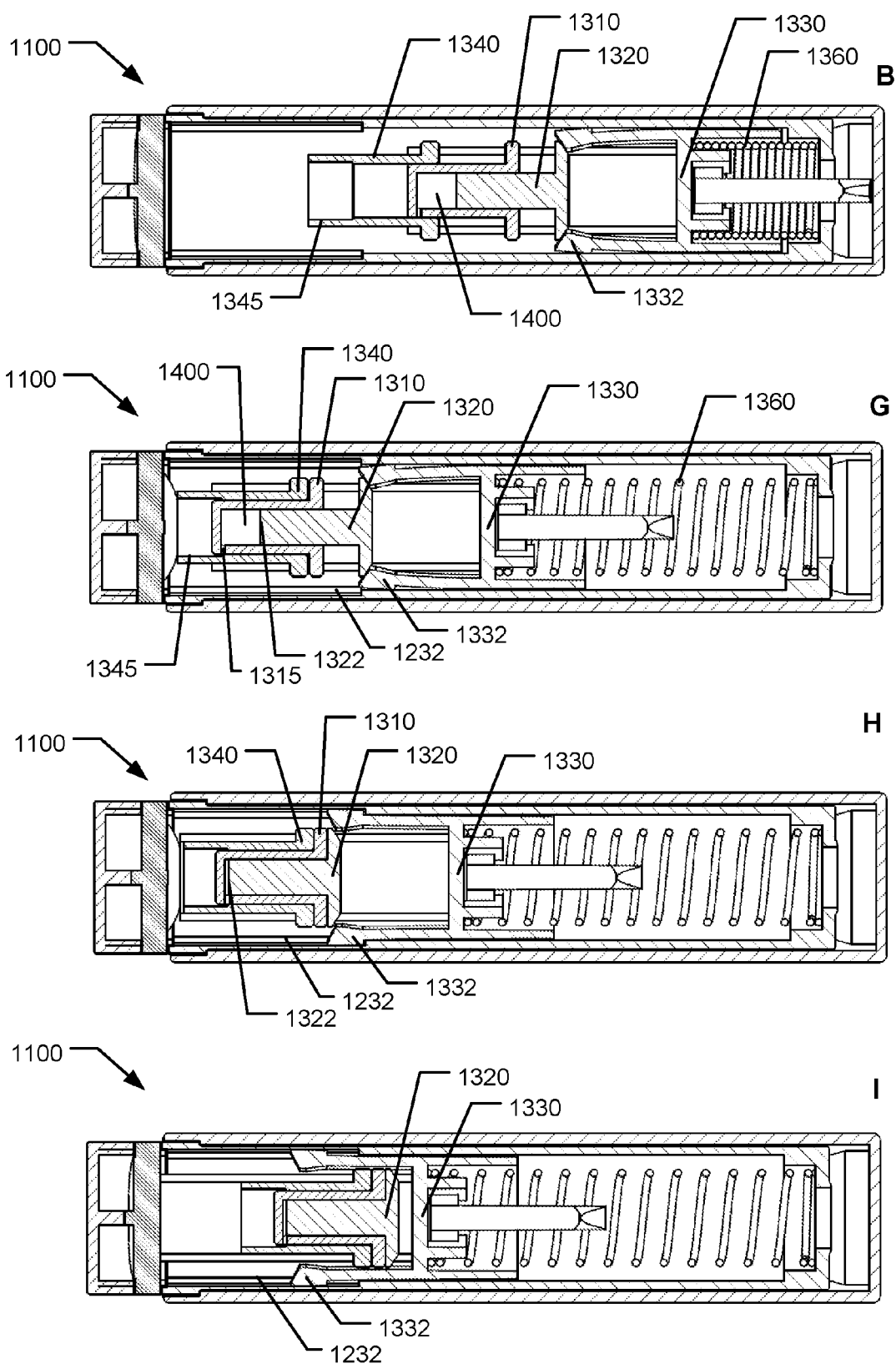
Figure 9A:
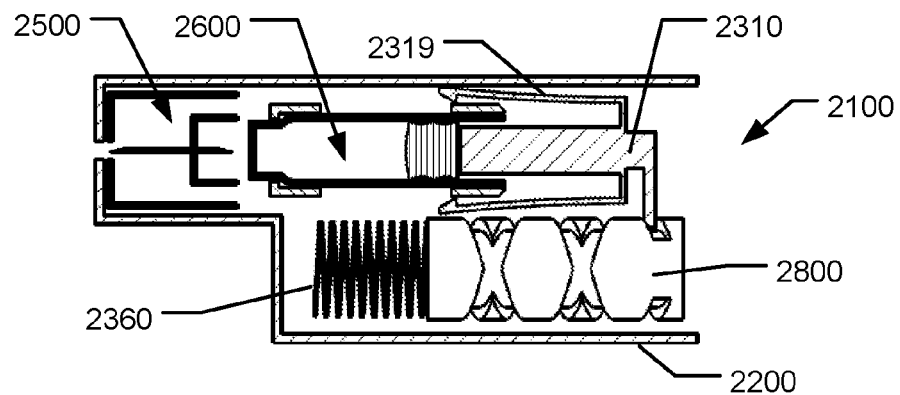
Figure 9B:
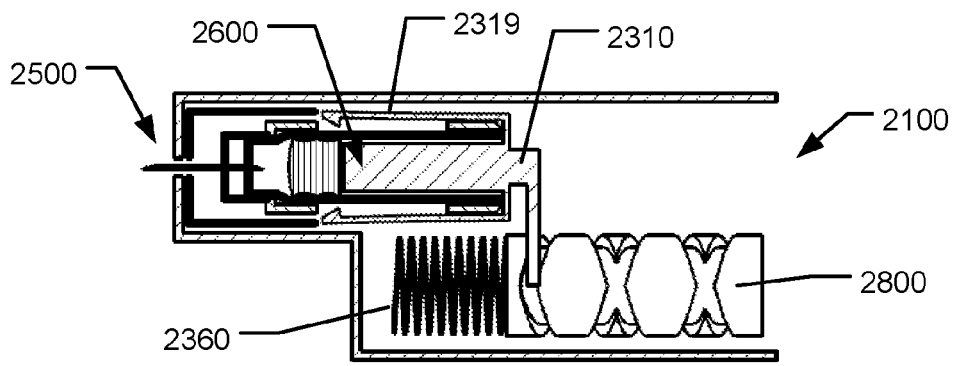
Figure 9C:
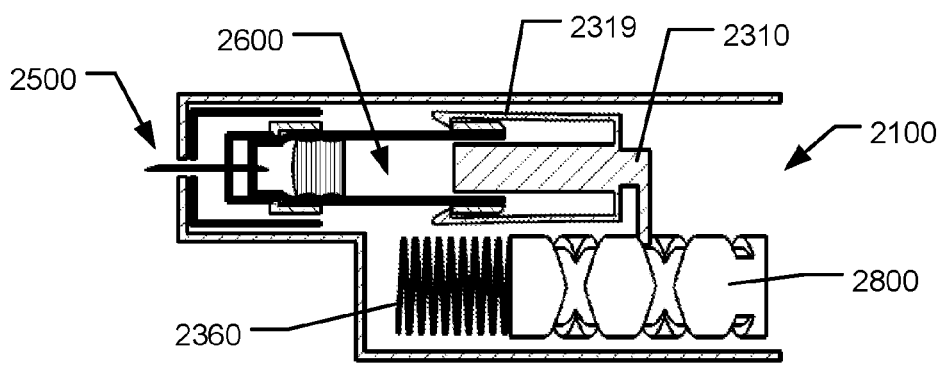
Figure 9D:
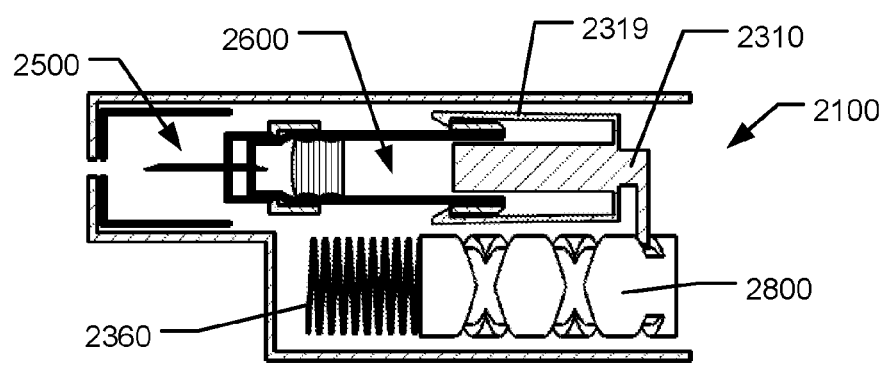

Continued movement of actuator thrust member 1330 pushes piston driver 1310 further distally relative to bushing member 1340 and hence drives piston 1630 relative to the body of cartridge 1600 until the piston driver 1310 is halted relative to the proximal end face 1611 of the cartridge body due to cooperation with a proximal flange section 1341 on bushing member 1340 (see state "G", FIGS. 8j and 8m). Hence, a fixed stroke length for the piston movement relative to body of cartridge 1600 is ensured in the same manner as described in connection with the first embodiment.

As best viewed in FIG. 8m, shortly before the device 1100 enters into state "G", the piston driver 1310 reaches a position relative to the bushing member 1340 where a control valve opens, i.e. where channel 1315 allows fluid communication to enlarged bore 1345 of bushing member 1340. Hence, continued pressure exerted by actuator thrust member 1330 on actuator connector 1320 forces an initially held fluid, such as an incompressible liquid, away from variable volume reservoir 1400 defined by distal face 1322 of actuator connector 1320 and an internal bore of piston driver 1310.

As indicated above, when actuator thrust member 1330 has moved to force the piston driver 1310 into its position where the end of stroke limiter 1611, 1341, 1311 has been activated, the damping mechanism is initiated. This facilitates further movement of actuator connector 1320 relative to the piston driver 1310. Upon lapse of the damping movement, the deflectable head portions 332 of actuator thrust member 1330 move radially outwards into respective track sections 1232 formed in housing 1200. Hereby actuator thrust member 1330 is coupled free from the engagement with the actuator connector 1320 (and the piston driver 1310), see FIG. 8m, state "H". This allows actuator thrust member 1330 to be thrust further in the distal direction where a trigger surface 1338 of the actuator thrust member 1330 induces force transfer member 1800 to rotate in the counter clockwise direction. This causes the force transfer member 1800 to rotate back to its first rotational position and thereby the needle assembly 1500 and cartridge 1600 is moved in the proximal direction, to render the front needle inaccessible (state "I", see FIGS. 8l and 8m).

Thus, in injection device 1100 a single spring acting in a compression mode is provided which provides energy for needle insertion, energy for expelling medicament and energy for withdrawing the needle.

A further not shown embodiment may be formed similar to the fifth embodiment but where the force transfer mechanism includes a hydraulic system with two cooperating pistons/cylinders which replaces the force transfer member 1800. In such an embodiment, the hydraulic system will switch the direction of movement from a distal directed movement to a proximal directed movement or vice versa.

In FIGS. 9a through 9d, a sixth embodiment of an injection device 2100 is shown which includes a cam mechanism with a torsion spring. This embodiment provides an actuator in the form of a pre-stressed torsion spring 2360 which may be released upon activation to cause a force transfer member in the form of a tubular member 2800 to rotate in a particular rotational direction. The tubular member is mounted fixedly axially in the housing 2200 to prevent translational movements but mounted so as to be rotatable around its central longitudinal axis which is arranged parallel to a central axis of the cartridge 2600. The piston driver 2310 is movable along the central axis of the cartridge 2600. The tubular member 2800 has a spiral track formed on the surface which includes two segments having opposed pitches. The piston driver 2310 in this embodiment includes a track follower adapted to follow the track segments of the tubular member 2800. The piston driver 2310 further includes a pair of retaining arms 2319 which snaps into engagement with the cartridge or the needle assembly when the piston driver moves towards the end of stroke position.

When the torsion spring 2360 is released, the track follower and hence the piston driver 2310 at first follows the first track segment and is moved in the distal direction. Hereby, the tubular member 2800 first drives the piston driver 2310 in the distal direction for facilitating the driving of the cartridge 2600 and the needle assembly 2500 distally for shifting the front needle into its unshielded state, then for moving the cartridge 2600 further in the distal direction for establishing fluid communication between cartridge 2600 interior and the needle cannula of the needle assembly 2500, and lastly drives the piston of the cartridge 2600 for expelling the medicament. When the track follower engages the second segment of the track formed in tubular member 2800, the piston driver 2310 is forced in the proximal direction of the device 2100. Due to the piston driver 2310 having engagement means (retaining arms 2319) for pulling the cartridge 2600 in the proximal direction when the piston driver 2310 is moved proximally, the cartridge 2600 and the needle assembly 2500 is moved proximally, thereby rendering the front needle inaccessible after the dose of medication has been administered.

In FIG. 10a through 10d, the working principle of a seventh embodiment of an injection device 3100 is schematically shown, the device 3100 having a flexible piston rod dose mechanism. This embodiment provides an actuator in the form of a pre-stressed linear compression spring 3360 which may be released upon activation to cause a piston driver 3310 to move. Piston driver 3310 has a base portion which is engaged with the compression spring 3360 and a piston rod part 3312 in the form a flexible piston rod which is guided in the housing to define a U-shaped configuration. From base portion of piston driver 3310, a proximally extending arm with a trigger surface 3318 extends towards a force transfer member 3800.

In this embodiment, the force transfer member is in the form of a guiding part 3800 which is adapted to be slideable movable relative to the housing 3200 in the proximal direction from the shown first position (FIG. 10a) to a second position (FIG. 10c) and further to a third position. The guiding part is initially retained in the first position but is released when the trigger surface 3338 of base portion of piston driver 3310 engages a not shown release mechanism allowing the guiding part to move proximally to its second position. Guiding part 3800 performs as a guide for the flexible piston rod 3310 using the same operating principle as shown in U.S. Pat. No. 5,957,889.

When the compression spring 3360 is released, during the initial movement of the flexible piston rod 3310, the end of the flexible piston rod that abuts the piston of the cartridge 3600 is driven in the distal direction for facilitating the driving of the cartridge 3600 and the needle assembly 3500 distally for shifting the front needle into its unshielded state, then for moving the cartridge 3600 further in the distal direction for establishing fluid communication between cartridge 3600 interior and the needle cannula of the needle assembly 3500, and lastly drives the piston of the cartridge 3600 for expelling the medicament. As shown in FIG. 10b, when the piston rod 3310 has reached a particular position relative to cartridge 3600 the trigger surface 3338 engages the release mechanism of the guiding part 3800, thereby allowing the guiding part 3800 to move proximally. Continued proximal movement of base part of piston driver 3310 pushes the guiding part 3800 proximally and thereby pulls by means of engagement means 3319 the cartridge 3600 in the proximal direction. Hence, as the cartridge 3600 and the needle assembly 3500 are moved proximally, the front needle is rendered inaccessible.

In FIG. 11a through 11e, the working principle of an eighth embodiment of an injection device 4100 is schematically shown, the device 4100 having a dosing mechanism incorporating an articulated piston rod configuration. As shown schematically in FIG. 10b, a piston driver 4310 is configured having two relatively rigid sections which are connected by a flexible shank. The proximal section of piston driver 4310 is coupled to a coiled spring which continuously exerts a torsion moment on a part of the proximal section. The distal section of piston driver 4310 serves as a piston rod for cooperating with a piston of cartridge 4600. Upon activation of the device 4100, the spring first drives the proximal segment to bend sideways as well as in the distal direction to the configuration shown in FIG. 11b, then to straighten up as shown in FIG. 11c, then. The distal segment of piston driver 4310 are hereby forced to drive firstly in the distal direction and subsequently in the proximal direction. When piston driver 4310 drives in the distal direction it drives the cartridge 4600 and the needle assembly 4500 distally for shifting the front needle into its unshielded state, then for moving the cartridge 4600 further in the distal direction for establishing fluid communication between cartridge 4600 interior and the needle cannula of the needle assembly 4500, and lastly drives the piston of the cartridge 4600 for expelling the medicament. When piston driver 4310 moves proximally, due to the piston driver 4310 having engagement means 4319 for pulling the cartridge 4600 in the proximal direction when the piston driver 4310 is moved proximally, the cartridge 4600 and the needle assembly 4500 is moved proximally, thereby rendering the front needle inaccessible.

A further working principle is shown in FIG. 12 which schematically represents the overall movement scheme of a ninth embodiment of an injection device 5100. Device 5100 includes a force transfer mechanism provided as a crank mechanism. Such an embodiment may include an actuator in the form of a pre-stressed torsion spring (not shown) which may be released upon activation to cause a force transfer member in the form of a crankshaft 5800 to rotate in a particular rotational direction. A piston driver 5610 forms a connecting rod which connects the piston of cartridge 5600 with the crankshaft 5800. As the crankshaft rotates, the piston driver 5610 is forced to move to cause a front needle of a needle assembly (not shown) to enter into its unshielded state, then to cause the cartridge 5600 to move further in the distal direction for establishing fluid communication between the interior of cartridge 5600 and a needle cannula of the needle assembly, then to cause the piston of the cartridge 5600 to expel a dose of the medicament held therein, and lastly to withdraw the needle assembly to render the front needle of the needle assembly inaccessible.

As described above, in the shown fifth to ninth embodiments, the force transfer mechanism is adapted for moving the needle assembly, in the last sequence, in a proximal direction to thereby render the needle inaccessible. However, in accordance with the operating principle of the third embodiment (according to the third aspect of the invention), the force transfer mechanism of the embodiments 5 to 9 may instead be adapted to drive the cartridge relative to the needle assembly from the state wherein the cartridge septum is pierced by the rear needle and wherein fluid is dispensable from the front needle into the second state where fluid flow from the cartridge to the rear needle is interrupted. In still other alternative embodiments, the force transfer mechanism may be adapted to drive the needle assembly relative to the cartridge from the state wherein the cartridge septum is pierced by the rear needle and wherein fluid is dispensable from the front needle into the second state where fluid flow from the cartridge to the rear needle is interrupted.

As discussed above, in the shown fifth to eighth embodiment, a pre-stressed spring is used which is exclusively loaded in a torsion load or a linear compression load and which upon activation drives the parts of the injection device during the various sequences. In comparison with prior art devices which use two or more springs for accomplishing the same level of automation, the cost of manufacturing an injection device according to the above described embodiments are considerable lowered, mainly due to the fact that springs are normally produced by a metal, whereas many other of the components may be manufactured by a much more inexpensive plastic material. This issue is of particular importance for disposable devices which permanently accommodates the medicament cartridge internally and which is disposed off after single use. Relative to the injection device shown in WO 2009/007305 which uses a single spring which is both prestressed with a torsion load and a linear load, the above described principle offers a reduced complexity during assembly. In a device shown in U.S. Pat. No. 7,717,877, this device also uses a single spring under compression load to accomplish automatic needle insertion, automatic dosing as well as automatic needle shielding. The needle shielding process occurs by means of the compression spring forces forward a shield relative to the main housing. However, the shielding process of that device utilizes the part of the spring compression where the spring force is comparatively low which may not provide sufficient force for an effective and fault-free shielding of the needle to take place.

Figure 13A:
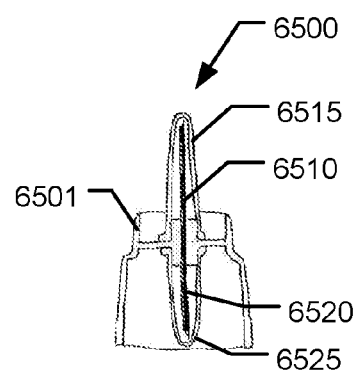
Figure 13B:
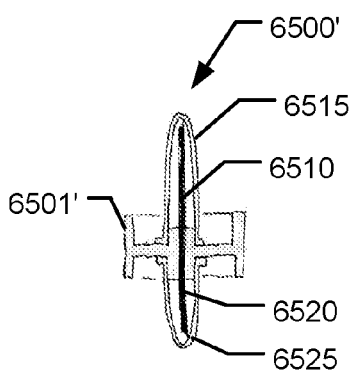

FIGS. 13a and 13b show two types of injection needles 6500 and 6500' according to the fifth aspect of the invention, the injection needles generally corresponding in function to the needle assembly shown in FIG. 3 and which may be incorporated in injection devices of the kind described above. The injection needles 6500, 6500' each comprises a needle hub 6501, 6501' having a front needle cannula part 6510 extending in a distal direction from the hub and having a rear needle cannula part 6520 extending in a proximal direction from the hub. The hub section 6501 shown in FIG. 13a has a design resembling conventional injection needles having a standard interface for cooperating with insulin injectors or the like, the interface being of the type providing a threaded section or a bayonet section, whereas the hub section 6501' shown in FIG. 13b has a design which is optimized for space saving solutions.

The injection needles 6500, 6500' includes front needle sheaths 6515 and rear needle sheaths 6525 respectively forming sterility sheaths for the front needle cannula part 6510 and the rear needle cannula part 6520. In the shown embodiment, the front and rear sterility sheaths are formed as rubber sheaths which are penetrable by the pointed tip of the respective needle cannula part. When the top portion of each respective sheath is forced towards the needle hub 6501, 6501' the pointed tips of the particular needle cannula part penetrates the sheath allowing the needle cannula part in question to be fully or partly exposed outside the needle sheath and hence ready for use. The front and rear needle cannula parts may be formed in one piece or separate pieces joined together for fluid communication. The front and rear needle sheaths may be formed as separate pieces or alternatively in one piece.

The needle cannula parts may be attached to the hub 6501, 6501' by gluing, interference fit or similar joining process. The front 6515 and rear sheath 6525 are attached to the hub 6501, 6501' either by gluing, welding, interference fit, a separate mounting element, or similar means. In the manufacturing process, after the two sheaths 6515, 6525 have been assembled to the hub section, they are in their extended positions in which they cover the front 6510 and rear needle cannula parts 6520 respectively.

Traditionally, during manufacture, such injection needles having penetrable sheaths covering the respective needle cannula parts have been handled and sterilized separately from other injection needles to avoid accidentally penetrating the sheaths.

In accordance with the fifth aspect of the present invention, each injection needle 6500, 6500' is inserted into a sterilizing compartment 6600, 6600' (see FIGS. 14a and 14b) to form a needle cannula assembly which allows subsequent sterilization, such as by steam sterilization of the entire needle cannula assembly.

Figures 14A, 14B:
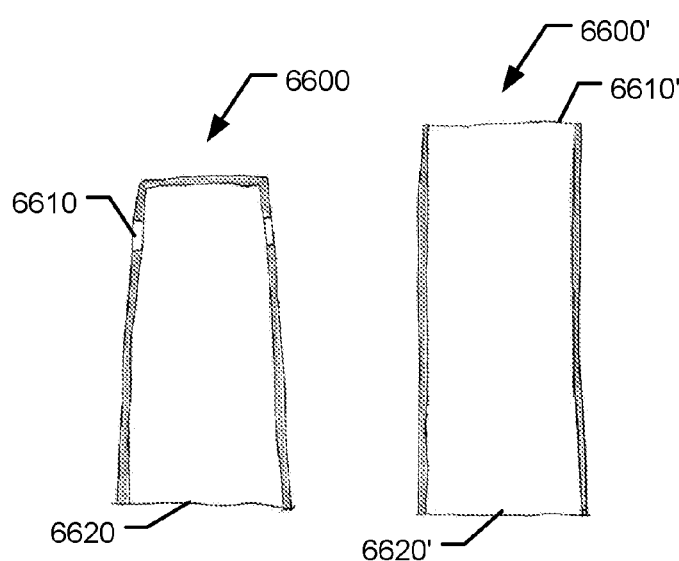
Figures 15A, 15B, 15C, 15D:
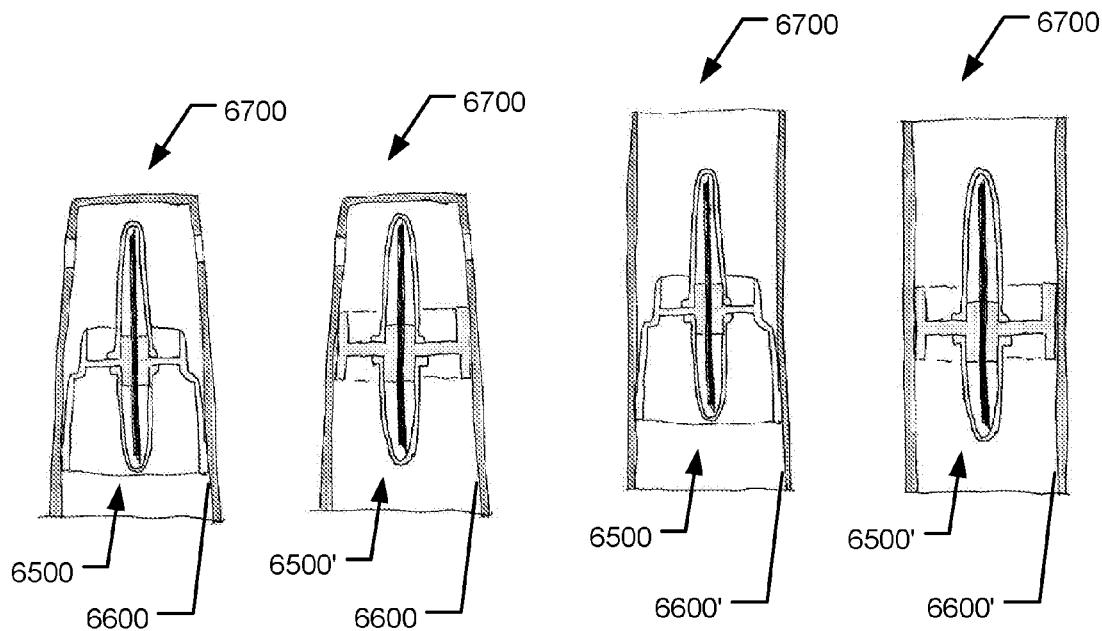
Figures 16A, 16B, 16C:
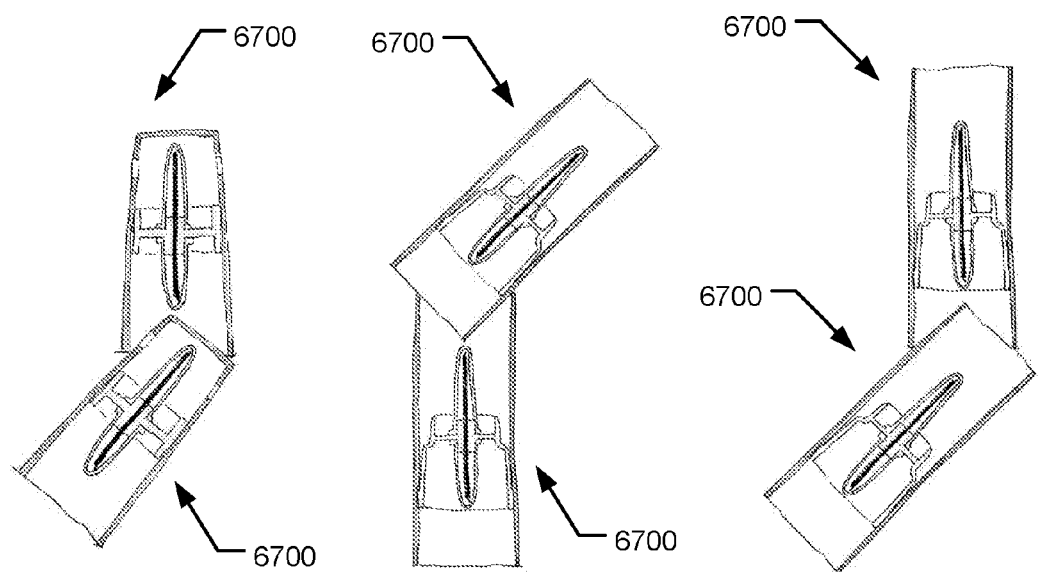

The sterilizing compartment 6600 shown in FIG. 14a provides a single large opening 6620 in the proximal end through which the injection needle 6500 or 6500' is inserted into and from which the injection needle may later be removed. The distal part of the sterilizing compartment 6600 may include one or more sterilizing openings to enable more effective sterilization of the entire injection needle 6500, 6500'. The sterilizing compartment 6600' shown in FIG. 14b provides one large opening 6620' in the proximal end and one large opening 6610' at the distal end. Both types of sterilizing compartment 6600, 6600' include means for retaining an inserted injection needle 6500, 6500' when inserted into the sterilizing compartment to enable an inserted injection needle to be effectively retained during a subsequent sterilizing process and or during subsequent handling. Any type of retaining means between the injection needle and its sterilizing compartment may be used, such as providing a friction fit coupling, a positive mechanical engagement such as a snap connection, a threaded connection or similar means.

FIGS. 15a, 15b, 15c and 15d show different combinations of injection needles 6500, 6500' and sterilizing compartments 6600, 6600' where each combination may be referred to as a needle cannula assembly 6700. Whatever combination is used the sterilizing compartment 6600 and 6600' is so formed that each of the needle sheaths 6515, 6525 is prevented from being touched by other similar needle cannula assemblies 6700 when bulk handling the needle cannula assemblies 6700. Examples of suitable configurations can be viewed in FIGS. 16a, 16b and 16c. By ensuring that the needle sheaths 6515, 6525 of each needle cannula assembly is not touched by other needle cannula assemblies, it is ensured that the needle sheaths are not accidentally urged to move relative to the pointed tip section of the respective needle cannula part 6510, 6520 and thereby not to become penetrated by the pointed tip. Hence, the risk of accidental sheath penetration is significantly reduced even when plural such needle cannula assemblies are sterilized by means of a bulk sterilization process and the sterility of the needles is kept uncompromised.

In some embodiments, the sterilizing compartment 6600, 6600' performs as a handling tool during subsequent handling and assembly operations. At some point during manufacture, the injection needle 6500, 6500' may be separated from its sterilizing compartment 6600, 6600' for example when assembling the needle with the injector in question. In other embodiments the sterilizing compartment forms part of the final injector. In some embodiments, the sterilizing compartment may serve as a needle holding means inside the housing of an injection device. In other embodiments, the sterilizing compartment may serve as a needle shield relative to which the injection needle is movable for rendering access to the tip of the front needle cannula part.

Some preferred embodiments have been shown in the foregoing, but it should be stressed that the invention is not limited to these, but may be embodied in other ways within the subject matter defined in the following claims.

The invention claimed is:

1. An injection device comprising:
   a medicament cartridge having an outlet covered by a cartridge septum adapted to be pierced by a needle for establishing fluid communication with the cartridge interior and having a slideably arranged piston which is driveable towards the outlet,
   a piston driver for engaging the piston and configured for driving the piston a predetermined stroke length towards the outlet of the cartridge,
   a needle holding structure,
   a needle assembly mounted on said needle holding structure, said needle assembly having a front needle for penetrating the skin of a subject user and a rear needle for piercing the cartridge septum, the cartridge and the needle assembly being configured for relative movement between a first state where the cartridge septum is pierced by the rear needle and where fluid communication is enabled into a second state where said fluid communication is interrupted, and
   an actuator coupled to the piston driver and driveable, when the cartridge septum is pierced by the rear needle, to cause the piston driver to move to dispense the medicament from the front needle in a dispensing operation,
   wherein the injection device further comprises a dispensing interruption mechanism adapted to actively shift by way of a relative movement the cartridge and the needle assembly from the first state wherein the cartridge septum is pierced by the rear needle and wherein fluid is dispensable from the front needle into the second state where fluid flow from the cartridge to the rear needle is interrupted, and
   wherein the dispensing interruption mechanism comprises a biasing structure adapted to urge the cartridge and the needle assembly towards the second state where the fluid communication is interrupted, wherein the dispensing interruption mechanism is so configured that the biasing structure actively shifts the cartridge and the needle assembly towards the second state responsive to the piston driver having moved the piston said predetermined stroke length to thereby automatically interrupt the dispensing operation.

2. An injection device as in claim 1, wherein the dispensing interruption mechanism comprises the biasing structure adapted to urge the cartridge and the needle assembly towards the second state where said fluid communication is interrupted, and wherein the dispensing interruption mechanism includes a retainer adapted to releasably retain the cartridge and the needle assembly in the state where the cartridge septum is pierced by the rear needle.

3. An injection device as in claim 2, wherein the device further comprises a housing and wherein the cartridge is mounted slideably relative to the housing for moving the cartridge away from the needle assembly upon release of said retainer.

4. An injection device as in claim 2, wherein the dispensing interruption mechanism further includes a retainer release trigger being associated with the piston driver and being adapted to cooperate with a retainer release surface associated with the retainer and adapted to release said retainer when the piston driver has moved into a predetermined position.

5. An injection device as in claim 1, wherein the device further comprises a housing and wherein the cartridge is retained in a cartridge holder mounted slideably relative to the housing for moving the cartridge away from the needle assembly.

6. An injection device as in claim 1, wherein the actuator includes a stored energy source capable of being released to cause the piston driver to move to dispense the medicament through the needle assembly.

7. An injection device as in claim 6, wherein the stored energy source is a single pre-stressed spring acting exclusively in a linear compression mode or exclusively in a torsion mode and wherein a force transfer mechanism transfers the force of the spring upon release sequentially in a first direction for:
   driving the piston driver for dispensing a dose of the medicament of the cartridge through the needle assembly,
   and in a second direction for:
   driving the cartridge relative to the needle assembly from the first state wherein the cartridge septum is pierced by the rear needle and wherein fluid is dispensable from the front needle into the second state where fluid flow from the cartridge to the rear needle is interrupted.

8. An injection device as in claim 2, wherein the device further includes an end of stroke limiter for arresting a piston driver in a pre-determined position relative to a proximally facing surface of the cartridge.

9. An injection device as in claim 8, wherein the piston driver has a first part which is coupled to the piston of the cartridge and a second part which is configured to move the first part during an injection stroke until the first part is arrested relative to the cartridge by way of the end of stroke limiter whereupon the second part is capable of further movement relative to first part for triggering release of said retainer.

10. An injection device as in claim 1, wherein the device comprises a housing, wherein the medicament cartridge is irremovably accommodated inside the housing and wherein the device is formed as a disposable device.

11. An injection device as in claim 10, wherein the device is adapted to deliver a single dose of a medicament for subsequent disposal.

* * * * *